US008187876B2

(12) United States Patent
Peled

(10) Patent No.: US 8,187,876 B2
(45) Date of Patent: *May 29, 2012

(54) EXPANSION OF STEM/PROGENITOR CELLS BY INHIBITION OF ENZYMATIC REACTIONS CATALYZED BY THE SIR2 FAMILY OF ENZYMES

(75) Inventor: Tony Peled, Mevasseret Zion (IL)

(73) Assignee: Gamida Cell Ltd., Jerusalem (IL)

( * ) Notice: Subject to any disclaimer, the term of this patent is extended or adjusted under 35 U.S.C. 154(b) by 797 days.

This patent is subject to a terminal disclaimer.

(21) Appl. No.: 11/631,992

(22) PCT Filed: Jul. 14, 2005

(86) PCT No.: PCT/IL2005/000753
§ 371 (c)(1),
(2), (4) Date: Jan. 8, 2007

(87) PCT Pub. No.: WO2006/006171
PCT Pub. Date: Jan. 19, 2006

(65) Prior Publication Data
US 2009/0004191 A1    Jan. 1, 2009

Related U.S. Application Data

(60) Provisional application No. 60/587,496, filed on Jul. 14, 2004.

(51) Int. Cl.
*C12N 5/08* (2006.01)
*C12N 5/00* (2006.01)
*C12N 5/02* (2006.01)

(52) U.S. Cl. .................. 435/372; 435/375; 435/377

(58) Field of Classification Search .................. None
See application file for complete search history.

(56) References Cited

U.S. PATENT DOCUMENTS 6,317,631 B1   11/2001   Ben-Haim et al. ................ 607/9
2007/0160586 A1   7/2007   Alt et al.

FOREIGN PATENT DOCUMENTS

WO   WO 03/062369   *  7/2003
WO   WO 2004/087885 A2   10/2004

OTHER PUBLICATIONS

Narala et al ( Molecular Biol. of the cell, 2008, v.19, pp. 1210-1219.*
Amsellem et al., "Ex vivo expansion of human hematopoietic stem cells by direct delivery of the HOXB4 homeoprotein", *Nat. Med.*, pp. 1-5 (2003).
Anderson et al., "Yeast Life-Span Extension by Calorie Restriction is Independent of NAD Fluctuation", *Science*, 302:2124-2126 (2003).
Avalos et al., "Structure of a Sir2 Enzyme Bound to an Acetylated p53 Peptide", *Mol. Cell*, 10:523-535 (2002).
Bedalov et al., "Identification of a small molecule inhibitor of Sir2p", *Proc. Natl. Acad. Sci. USA*, 98(26):15113-15118 (2001).
Bhatia et al., "Purification of primitive human hematopoietic cells capable of repopulating immune-deficient mice", *Proc. Natl. Acad. Sci. USA*, 94:5320-5325 (1997).
Blander et al., "The SIR2 Family of Protein Deacetylases", *Annu. Rev. Biochem.*, 73:417-435 (2004).
Chen et al., "Differentiation of rat marrow mesenchymal stem cells into pancreatic islet beta-cells", *World J. Gastroenterol.*, 10(20):3016-3020 (2004).
Grozinger et al., "Identification of a Class of Small Molecule Inhibitors of the Sirtuin Family of NAD-dependent Deacetylases by Phenotypic Screening", *J. Biol. Chem.*, 276(42):38837-38843 (2001).
Hirao et al., "Identification of Selective Inhibitors of $NAD^+$-dependent Deacetylases Using Phenotypic Screens in Yeast", *J. Biol. Chem.*, 278(52):52773-52782 (2003).
Hisahara et al., "Effects of Histone Deacetylase $SIR2\alpha$ on Proliferation and Differentiation of Neural Stem Cells", *Society for Neuroscience*, Program No. 242.12 (2003) (Abstract Only).
Horio et al., "Functional analysis of SIR2", *Folia Pharmacol. Jpn.*, 122(Suppl. 1):30P-32P (2003) (English Abstract Only).
Inden et al., "Pharmacological Characteristics of Rotational Behavior in Hemiparkinsonian Rats Transplanted With Mouse Embryonic Stem Cell-Derived Neurons", *J. Pharmacol. Sci.*, 96:53-64 (2004).
Kyrylenko et al., "Differential regulation of the Sir2 histone deacetylase gene family by inhibitors of class I and II histone deacetylases", *Cell. Mol. Life Sci.*, 60:1990-1997 (2003).
Landry et al., "The silencing protein SIR2 and its homologs are NAD-dependent protein deacetylases", *Proc. Natl. Acad. Sci. USA*, 97(11):5807-5811 (2000).
Lin et al., "Requirement of NAD and SIR2 for Life-Span Extension by Calorie Restriction in *Saccharomyces cerevisiae*", *Science*, 289:2126-2128 (2000).
McBurney et al., "The Absence of $SIR2\alpha$ Protein Has No Effect on Global Gene Silencing in Mouse Embryonic Stem Cells", *Mol. Cancer Res.*, 1:402-409 (2003).
McBurney et al., "The Mammalian $SIR2\alpha$ Protein Has a Role in Embryogenesis and Gametogenesis", *Mol. Cell. Biol.*, 23(1):38-54 (2003).
Motta et al., "Mammalian SIRT1 Represses Forkhead Transcription Factors", *Cell*, 116:551-563 (2004). Ng et al., "Selective in vitro expansion and efficient retroviral transduction of human $CD34^+$ $CD38^-$ haematopoietic stem cells", *Br. J. Haematol.*, 117:226-237 (2002).
Tanner et al., "Silent information regulator 2 family of NAD-dependent histone/protein deacetylases generates a unique product, 1-O-acetyl-ADP-ribose", *Proc. Natl. Acad. Sci. USA*, 97(26):14178-14182 (2000).
Tanny et al., "An Enzymatic Activity in the Yeast Sir2 Protein that is Essential for Gene Silencing", *Cell*, 99:735-745 (1999).
Travers et al., "Human CD34+ Hematopoietic Progenitor Cells Hyperacetylate Core Histones in Response to Sodium Butyrate, but Not Trichostatin A", *Exp. Cell Res.*, 280(2) 149-157 (2002).
Yeung et al., "Modulation of NF-κB-dependent transcription and cell survival by the SIRT1 deacetylase", *Embo J.*, 23(12):2369-2380 (2004).
Zheng et al., "γ-Catenin contributes to leukemogenesis induced by AML-associated translocation products by increasing the self-renewal of very primitive progenitor cells", *Blood*, 103(9):3535-3543 (2004).

(Continued)

*Primary Examiner* — Michail Belyavskyi
(74) *Attorney, Agent, or Firm* — Mintz Levin Cohn Ferris Glovsky and Popeo, P.C.; Ivor R. Elrifi; Matthew Pavao

(57) ABSTRACT

Provided are ex vivo and in vivo methods of expanding renewable stem cells using agents capable of down-regulating Sir2 protein activity and/or expression, expanded populations of renewable stem cells, and uses thereof.

14 Claims, 8 Drawing Sheets

OTHER PUBLICATIONS

Communication Relating to the Results of the Partial International Search Dated Nov. 24, 2005 From the International Searching Authority Re.: Application No. PCT/IL2005/000753.

International Preliminary Report on Patentability Dated Jan. 25, 2007 From the International Bureau of WIPO Re.: Application No. PCT/IL2005/000753.

International Search Report and the Written Opinion Dated Feb. 20, 2006 From the International Searching Authority Re.: Application No. PCT/IL2005/000753.

Horio et al., "Histone decetylase Sir2α affects proliferation and differentiation of neural stem cells", *J. Pharmacol., Sci.*, 94(Suppl.1) 49 (2004).

Fulco et al., "Sir2 Regulates Skeletal Muscle Differentiation as a Potential Sensor of the Redox State", *Molecular Cell* 12:51-62 (2003).

Huang et al., "SIRT1 Overexpression Antagonizes Cellular Senescence with Activated ERK/S6k1 Signaling in Human Diploid Fibroblasts", *PLoS One* 3(3):1-9 (2008).

Langley et al., "Human SIR2 deacetylates p53 and antagonizes PML/p53-induced cellular senescence", The EMBO J. 21(10):2383-2396 (2002).

Li et al., "Cell Life Versus Cell Longevity: The Mysteries Surrounding the NAD+ Precursor Nicotinamide" *Curr. Med. Chem* 13(8):883-895 (2006).

Picard et al., "Sirt1 promotes fat mobilization in white adipocytes by repressing PPAR-y", *Nature* 429(6993):1-14 (2004).

\* cited by examiner

FACS analysis: CD34/Lin

Control-cytokines only

| Quad | % Gated |
|------|---------|
| UL | 0.02 |
| UR | 99.08 |
| LL | 0.05 |
| LR | 0.85 |

Nicotinamide 5mM

| Quad | % Gated |
|------|---------|
| UL | 16.58 |
| UR | 80.08 |
| LL | 0.05 |
| LR | 3.29 |

FACS analysis: 34/HLA-DR+38

EXPANSION OF STEM/PROGENITOR CELLS BY INHIBITION OF ENZYMATIC REACTIONS CATALYZED BY THE SIR2 FAMILY OF ENZYMES

RELATED APPLICATIONS

This application is a 35 U.S.C. §371 National Phase Application of PCT/IL2005/000753, filed Jul. 14, 2005; which claims priority from U.S. Ser. No. 60/587,496 filed Jul. 14, 2004, each of which is incorporated by reference in its entirety.

FIELD AND BACKGROUND OF THE INVENTION

The present invention relates to methods of expansion of renewable stem cells, to expanded populations of renewable stem cells and to their uses. The present invention further relates to therapeutic applications in which these methods and/or the expanded stem cells populations obtained thereby are utilized.

In vitro expansion of hematopoietic stem-progenitor cells (HSPCs) is constrained by default pathways of commitment and differentiation. Exposure of progenitor cells to different combinations of cytokines supports their exit from the $G_0/G_1$ phase of the cell cycle and enables extensive proliferation. However, such proliferation is tightly coupled with commitment and differentiation rather than self-renewing division [Avalos et al. (2002) Mol. Cell. 10:523-535]. Uncoupling of these cellular events by genetic manipulations may lead to uncontrolled cell proliferation and eventually to cell transformation [Zheng Blood (2004) 103(9):3535-43].

To overcome these limitations, attempts are constantly made to identify modulators that can create an environment that favors HSPCs self-renewal with only limited differentiation, in vitro [Amsellem Nat. Med. (2003) 9(11): 1423-7].

The sitruin family of enzymes (also termed, SIRs (for Silent Information Regulators); and Sir-2/Sir2) constitute the class III of deacetylases. These enzymes are conserved in many organisms ranging from bacteria to humans. The founding member of this family, yeast Sir2, has been found in multiprotein complexes and is required for gene silencing in yeast. The functions of human sirtuins have not yet been determined. However, recent studies suggest that the human sirtuins may function as intracellular regulatory proteins with mono-ADP-ribosyltransferase activity.

SIRT family members can be recognized in BLAST searches due to the presence of a conserved core of about 203 amino acid (aa) residues. The archaebacterial family members are not much larger than this core, ranging in size from 245 to 253 aa in length. The eubacterial members are more divergent in length, ranging in size from 208 residues (Actinobacillus actinomycetemcomitans) to 299 residues (Streptomyces), with more variation in the N- and C-terminal extensions. Mammalian SIRT2 is a protein not much larger than the largest prokaryotic SIRT protein. It is, however, considerably smaller than the founding member, Sir2, which is 562 residues in length. Human Sir2 comprise 7 isoforms (i.e., SIRT1-7): these forms are similar in size to Hst2 from budding yeast (357 residues). Like Hst2, mammalian hSIRT2 is a cytoplasmic protein [Afsha (1999) Gene 234:161-168; Perrod (2001) EMBO J. 20:197-209; Yang (2000) Genomics 69:355-3695], while hSIRT3 is a mictochondrial protein.

The conserved core of Sir2 proteins (about 203 residues, approximately 24 kDa) folds into an $NAD^+$-binding protein with intrinsic protein deacetylase activity capable of removing the acetyl moiety from the $\epsilon$-amino group of lysine residues in protein substrates, including the N terminus of histone H4 and the C terminus of p53. This apparent deacetylase activity of SIRT proteins differs from the histone deacetylase (HDAC, classes I and II) activity of other mammalian and yeast HDACs in its insensitivity to trichostatin A (TSA), insensitivity to sodium butyrate, and strict requirement for $NAD^+$ as a cofactor (see FIGS. 1a-b).

The unique catalytic reaction catalyzed by Sir2-like requires the co-enzyme NAD+ (FIG. 1b). In this reaction, nicotineamide is liberated from NAD+ and the acetyl group of the substrate is transferred to cleaved NAD+, generating the novel metabolite O-acetyl-ADP ribose (OAADPr). This final product as well as ADP-ribose, when injected into starfish oocytes or blastomeres, induces a delay or complete blockage of the cell cycle during development [Borra (2002) J. Biol. Chem. 277:12632-12641]. Production of OAAR by SIRT proteins is coupled closely to NAD-dependent deacetylase (NDAC) activity, which raises the possibility that OAAR may act as a second messenger, electing a yet unknown reaction.

The protein deacetylase function presumed to be intrinsic to all SIRT proteins may be their functional commonality. While the chromatin remodeling properties of Sir2 (resulting from histone deacetylation) in the budding yeast may be atypical of SIRT proteins, as might be expected from the fact that SIRT genes exist in prokaryotes that are devoid of histones. Presumably, eukaryotic SIRT proteins all share the NDAC activity, but differ in their cellular function due to general subcellular distribution and specific protein-protein interactions with their acetylated protein substrates, properties that would be unique to each SIRT ortholog and presumably determined by the folding of the N- and C-terminal extensions as Avalos et al. (supra) have recently suggested. It would not be surprising to find functions for mammalian SIRT proteins that supersede chromatin remodeling.

Recently, it has been suggested that the deacetylase activity SIRT family of enzymes is not restricted to histone protein substrates [Buck (2004) 75(6):939-50].

Indeed, a distant homologue of Sir2 called CobB is found in Salmonella typhimurium, which do not have histones, where it can compensate for the loss of the phosphoribosyltransferase, CobT, suggesting a ribosyltransferase activity. Recent findings also support the concept that nonhistone proteins can serve as substrates for Sir2-like proteins in mammalian cells. For example, it has been shown that human Sir proteins deactylate transcription factors, thereby regulating transcriptional activity. hSIRT1 deacetylates the transcription factor p53 and inhibits its activation in response to DNA damage and oxidative stress. Mouse Sir2α deacetylates the $TAF_I68$ subunit of the TATA-box binding protein-containing factor, leading to the repression of RNA polymerase I transcription.

NF-kappaB is responsible for upregulating gene products that control cell survival. SIRT proteins regulates the transcriptional activity of NF-kappaB. SIRT1 physically interacts with the RelA/p65 subunit of NF-kappaB and inhibits transcription by deacetylating RelA/p65 at lysine 310 [Yeung EMBO J. (2004) 23(12):2369-80]. Treatment of cells with resveratrol, a small-molecule agonist of Sirtuin activity, potentiates chromatin-associated SIRT1 protein on the cIAP-2 promoter region, an effect that correlates with a loss of NF-kappaB-regulated gene expression and sensitization of cells to TNFα-induced apoptosis. While SIRT1 was suggested to be capable of protecting cells from p53-induced apoptosis it's activity augments apoptosis in response to TNFα by the ability of the deacetylase to inhibit the transactivation potential of the RelA/p65 protein [Yeung EMBO J. (2004) 123(12):2369-80].

Another example is the Chicken homolog of Sir-2, chicken ovalbumin upstream promoter transcription factor (COUP-TF)-interacting proteins 1 and 2 (CTIP1 and CTIP2) which enhance transcriptional repression mediated by COUP-TF II and have been implicated in hematopoietic cell development and malignancies. The effects of CTIP1 and CTIP2 CTIP2-mediated transcriptional repression, as well as deacetylation of promoter-associated histones H3/H4 in CTIP2-transfected cells, is reversed by nicotineamide, indicating transcriptional control activity of the chicken homolog. Interestingly, the human homolog of yeast Sir2, SIRT1, was found to interact directly with CTIP2 and was recruited to the promoter template in a CTIP2-dependent manner. Moreover, SIRT1 enhanced the deacetylation of template-associated histones H3/H4 in CTIP2-transfected cells, and stimulated CTIP2-dependent transcriptional repression. Finally, endogenous SIRT1 and CTIP2 co-purified from Jurkat cell nuclear extracts in the context of a large (1-2 mDa) complex. These findings implicate SIRT1 as a histone H3/H4 deacetylase in mammalian cells and in transcriptional repression mediated by CTIP2 [Senawong J Biol. Chem. 2003; 278(44):43041-50].

It was suggested that the SIR2 proteins are histone ADP-ribosyltransferases [Tanny (1999) Cell 99, 735-745], histone/protein deacetylases [Landry (2000) Proc. Natl. Acad. Sci. USA 97, 5807-5811], or both [Kirk Proc Natl Acad Sci USA. 2000 Dec. 19; 97 (26): 14178-14182].

This unique and tightly coupled reaction mediated by these enzymes It is well established that many NAD-dependent enzymes (NAD$^+$ glycohydrolases, ribosyltransferases, and ADP-ribosyl cyclases) form a putative oxocarbenium ADP-ribose cation as the direct product of nicotinamide elimination. Given this precedent for oxocarbenium cation formation and the previously observed NAD$^+$-nicotinamide exchange reaction, SIR2 enzymes will likely form a similar intermediate. Interestingly, in the case of the SIR2 enzymes, oxocarbenium cation formation seems to require acetyl-lysine binding (and/or deacetylation). Only in the presence of acetyl-lysine and NAD$^+$ can exogenously added nicotinamide exchange with the enzyme intermediate to reform NAD$^+$.

Two possible chemical mechanisms for catalysis by the SIR2 family have been proposed. In both cases, a putative oxocarbenium ADP-ribose intermediate is formed by the elimination of nicotinamide from NAD$^+$. In the first mechanism, formation of the oxocarbenium is coupled to acetyl-lysine binding or hydrolysis. On acetyl-lysine hydrolysis, enzyme-bound acetate attacks the oxocarbenium cation to produce 1-O-acetyl-ADP-ribose. Alternatively, acetyl-lysine condenses directly with the oxocarbenium cation. This mechanism would imply that acetyl-lysine binding induces the elimination of nicotinamide to form initially the oxocarbenium intermediate. The acyl oxygen of acetyl-lysine condenses with the oxocarbenium cation. A hydroxide ion then attacks this intermediate to form a tetravalent intermediate, Which can collapse to produce 1-O-acetyl-ADP-ribose through the use of enzyme general acid/base catalysis. Although unlikely based on the above arguments, a different isomer of 1-O-acetyl-ADP-ribose may be formed. It was suggest that the reported histone/protein ADP-ribosyltransferase activity is a low-efficiency side reaction that can be explained through the partial uncoupling of the intrinsic deacetylation/acetate ADP-ribosylation reactions. The fact that these enzymes are capable of an NAD$^+$-nicotinamide exchange reaction suggests that the oxocarbenium cation of ADP-ribose is at least partially susceptible to attack by the base nucleophile. However, the proposed oxocarbenium cation of SIR2 enzymes seems to be exquisitely constructed to limit other possible side reactions, such as attack by H$_2$O or by nucleophilic amino acid side chains, which would result in ADP-ribose or protein ADP-ribosylation, respectively. At most, protein ADP-ribosylation that is about 0.1% of the authentic reaction. Also, ADP-ribose was not detected as a primary enzymatic product. It may be possible that some uncoupling of this reaction to yield protein ADP-ribosylation could result from perturbations in native protein structure (partially unfolded protein, mutagenesis, inappropriate reaction conditions) and from extremely high concentrations of an alternate acceptor, such as reactive protein side chains.

It is suggested that 1-O-acetyl-ADP-ribose, a previously unknown molecule, has a unique cellular function or functions that may be linked to SIR2's gene-silencing effects, raising the possibility that 1-O-acetyl-ADP-ribose has an important signaling role in which other enzymes/proteins may use 1-O-acetyl-ADP-ribose to elicit the proper cellular response. Such targets might include ATP-dependent chromatin remodeling enzymes, histone/protein acetyltransferases, or poly(ADP-ribosyl)transferases. It is interesting to note that poly(ADP-ribosyl)transferases use NAD$^+$ to poly (ADP-ribosyl)ate proteins involved in the metabolism of nucleic acids and in the maintenance of chromatin architecture. One intriguing possibility is that 1-O-acetyl-ADP-ribose could bind poly(ADP-ribosyl)transferases and block poly(ADP ribosyl)ation. Moreover, NAD$^+$ levels in cells are inversely affected by the level of protein poly(ADP-ribosyl) ation. Because poly(ADP-ribosyl)transferases and SIR2 enzymes exhibit similar K$_m$ values (about 50-70 µM) for NAD$^+$, they may compete for the available NAD$^+$ and oppose each other's function. Recently, the observation has been made that caloric restriction leading to increased life span seems to be linked through an NAD$^+$- and SIR2-dependent pathway, which raises the possibility that 1-O-acetyl-ADP-ribose may play a role in this phenomenon. It is important to note that bacteria do not have histones, and yet they do have SIR2-like proteins with similar activity, as has been shown here for HST2/SIR2/CobB. Thus, histones need not be the only substrates for deacetylation by these enzymes. Identification of the authentic products and the catalytic mechanism of the SIR2-like enzymes has provided the initial basis for understanding the cellular role(s) played by this important family of proteins. [Cakir (2000). Science 289, 2126-2128].

A number of Sir2 catalytic inhibitors are known, displaying various affinities towards the different Sirtuin family members (i.e., cross-species). Examples include Nicotineamide, Sirtinol and derivatives of the same, Splitomicin and derivatives of the same [Bedalov Proc Natl Acad Sci USA. 2001 98(26):15113-8; Hirao J Biol Chem. (2003) December 26; 278(52):52773-82]. Interestingly, SIR inhibitors and HDAC inhibitors exert different biological activities indicating an activity of SIR different then histone deacetylase [Grozinger J. Biol. Chem., Vol. 276, Issue 42, 38837-38843, (2001)].

Biological activity of the SIR family of enzymes has been implicated in metabolism regulation and aging. Sir2 activation was shown to extend the life-span of yeast under calorie restriction. Similar results were obtained in C. elegans were Sir2 was found to regulate life span through activation of the forkhead transcription factor DAF-16, which is required for longevity [Lin (2000) Science 289:2126-2128]. Indeed, inhibition of Sir-2 was suggested for increasing life-span by controlling stress-resistance of cells (see e.g., WO 2004/016726).

Sir2 was also found to interact with acetyl-transferase PCAF and formed a complex with MyoD. Sir2 transfers the acetyl groups carried by DCAF to MyoD in a NAD+-dependent manner. Over-expression of Sir2 inhibits muscle gene expression and differentiation [Anderson (2003) Science 302:2124-2126]. However, the role of SIRs in events associated with stem cell differentiation is yet poorly understood.

Self-renewal of hemopoietic stem and progenitor cells (HPC) both in vivo and in vitro is limited by cell differentiation. Differentiation in the hematopoietic system involves, among other changes, altered expression of surface antigens [Sieff (1982) Blood 60:703]. In normal human, most of the hematopoietic pluripotent stem cells and the lineage committed progenitor cells are CD34+. The majority is CD34+ CD38+, with a minority (<10%) being CD34+CD38−. The CD34+CD38− phenotype appears to identify the most immature hematopoietic cells, which are capable of self-renewal and multilineage differentiation. The CD34+CD38− cell fraction contains more long-term culture initiating cells (LTC-IC) pre-CFU and exhibits longer maintenance of their phenotype. and delayed proliferative response to cytokines as compared to CD34+CD38+ cells. CD34+CD38− can give rise to lymphoid and myeloid cells in vitro and have an enhanced capacity to repopulate SCID mice [Bhatia (1997) Proc Natl Acad Sci USA 94:5320]. Moreover, in patients who received autologous blood cell transplantation, the number of CD34+CD38− cells infused correlated positively with the speed of hematopoietic recovery. In line with these functional features, CD34+CD38− cells have been shown to have detectable levels of telomerase.

Based on the above descriptions, it is clear that there is thus a widely recognized need for, and it would be highly advantageous to have, a method of propagating large numbers of stem cells in an ex-vivo setting. Methods enabling ex-vivo expansion of stem cell compartments yielding large numbers of these cell populations will therefore pioneer feasible stem cell therapies for human treatment, with a clear and direct impact on the treatment of an infinite number of pathologies and diseases. Some pathological and medically induced conditions are characterized by a low number of in-vivo self or transplanted renewable stem cells, in which conditions, it will be advantageous to have an agent which can induce stem cell expansion in-vivo.

SUMMARY OF THE INVENTION

According to one aspect of the present invention there is provided a method of expanding and inhibiting differentiation of a population of stem cells, the method comprising providing the stem cells with an agent capable of down-regulating activity and/or expression of a Sir2 protein and/or a down-stream effector of the Sir2 protein, thereby expanding and inhibiting differentiation of the population of stem cells.

According to further features in preferred embodiments of the invention described below, expanding and inhibiting differentiation of the population of stem cells is effected ex-vivo.

According to still further features in the described preferred embodiments the ex-vivo expanding and inhibiting differentiation of the population of stem cells is effected by: (a) providing the stem cells ex vivo with conditions for cell proliferation; (b) ex vivo expanding the stem cells with the agent, thereby ex vivo expanding and inhibiting differentiation of the population of stem cells.

According to still further features in the described preferred embodiments the expanding and inhibiting differentiation of the population of stem cells is effected in-vivo.

According to still further features in the described preferred embodiments the stem cells comprise early hematopoietic cells and/or hematopoietic progenitor cells.

According to still further features in the described preferred embodiments the conditions are selected from the group consisting of a growth medium, differentiation chemical inhibitors and cytokines.

According to still further features in the described preferred embodiments the differentiation chemical inhibitors are selected from the group consisting of nicotineamide, PI-3 Kinase inhibitors and RAR antagonists.

According to still further features in the described preferred embodiments the cytokines are selected from the group consisting of early acting cytokines and late acting cytokines.

According to still further features in the described preferred embodiments the early acting cytokines are selected from the group consisting of stem cell factor, FLT3 ligand, interleukin-6, thrombopoietin and interleukin-3.

According to still further features in the described preferred embodiments the late acting cytokines are selected from the group consisting of granulocyte colony stimulating factor, granulocyte/macrophage colony stimulating factor and erythropoietin.

According to still further features in the described preferred embodiments the stem cells are derived from a source selected from the group consisting of hematopoietic cells, neural cells, oligodendrocyte cells, skin cells, hepatic cells, embryonal stem cells, muscle cells, bone cells, mesenchymal cells, pancreatic cells, chondrocytes and stroma cells.

According to still further features in the described preferred embodiments the stem cells are derived from bone marrow or peripheral blood.

According to still further features in the described preferred embodiments the stem cells are derived from neonatal umbilical cord blood.

According to still further features in the described preferred embodiments the population of stem cells are enriched for hematopoietic stem cells.

According to another aspect of the present invention there is provided a method of transducing expanded, undifferentiated stem cells with an exogene, the method comprising: (a) obtaining a population of stem cells; (b) expanding and inhibiting differentiation of the stem cells by: (i) providing the stem cells with conditions for cell proliferation; (ii) providing the stem cells with an effective concentration of at least one agent capable of down-regulating activity and/or expression of a Sir2 protein and/or a down-stream effector of the Sir2 protein, wherein steps (i) and (ii) are effected in vitro or ex vivo, thereby expanding and inhibiting differentiation of the stem cells; and (c) transducing the expanded, undifferentiated stem cells with the exogene.

According to still further features in the described preferred embodiments the transducing is effected by a vector comprising the exogene.

According to still further features in the described preferred embodiments the method further comprising the step of selecting a population of stem cells enriched for hematopoietic stem cells.

According to still further features in the described preferred embodiments the selecting is affected via CD34.

According to still further features in the described preferred embodiments the method further comprising the step of selecting a population of stem cells enriched for early hematopoietic stem/progenitor cells.

According to still further features in the described preferred embodiments the selection is affected via CD133.

According to yet another aspect of the present invention there is provided an isolated undifferentiated stem cell population characterized by down regulated activity and/or expression of a Sir2 protein or a down-stream effector of the Sir2 protein.

According to still another aspect of the present invention there is provided a therapeutic ex vivo cultured stem cell population comprising undifferentiated hematopoietic cells expanded according to the methods described herein.

According to an additional aspect of the present invention there is provided a cell culture comprising the stem cell population comprising undifferentiated hematopoietic cells expanded according to the methods described herein, a culture medium and at least one agent capable of down-regulating activity and/or expression of a Sir2 protein and/or a down-stream effector of the Sir2 protein.

According to yet an additional aspect of the present invention there is provided a pharmaceutical composition comprising as an active ingredient the stem cell population comprising undifferentiated hematopoietic cells expanded according to the methods described herein and a pharmaceutically acceptable carrier.

According to still an additional aspect of the present invention there is provided a method of transplanting hematopoietic stem cells in a recipient, the method comprising: (a) obtaining a population of hematopoietic stem cells; (b) ex vivo expanding and inhibiting differentiation of the hematopoietic stem cells by: (i) ex vivo providing the hematopoietic stem cells with conditions for cell proliferation; (ii) providing the hematopoietic stem cells ex vivo with an effective concentration of at least one agent capable of down-regulating activity and/or expression of a Sir2 protein and/or a down-stream effector of the Sir2 protein; thereby expanding and inhibiting differentiation of the stem hematopoietic cells; and (c) transplanting the hematopoietic stem cells into the recipient.

According to still an additional aspect of the present invention there is provided a method of adoptive immunotherapy comprising: (a) obtaining progenitor hematopoietic cells from a patient; (b) ex vivo expanding and inhibiting differentiation of the hematopoietic cells by: (i) providing the progenitor hematopoietic cells ex vivo with conditions for cell proliferation; (ii) providing the progenitor hematopoietic cells with an effective concentration of at least one agent capable of down-regulating activity and/or expression of a Sir2 protein and/or a down-stream effector of the Sir2 protein; thereby expanding and inhibiting differentiation of the progenitor hematopoietic cells; and (c) transplanting the progenitor hematopoietic cells into a recipient.

According to a further aspect of the present invention there is provided a method of mobilizing bone marrow stem cells into the peripheral blood of a donor for harvesting the cells comprising: (a) administering to the donor an effective concentration of at least one agent capable of down-regulating activity and/or expression of a Sir2 protein and/or a down-stream effector of the Sir2 protein, thereby expanding and inhibiting differentiation of a population of bone marrow stem cells; and (b) harvesting the cells by leukopheresis.

According to yet a further aspect of the present invention there is provided a method of adoptive immunotherapy comprising: (a) obtaining progenitor hematopoietic cells from a patient; (b) ex vivo expanding and inhibiting differentiation of the hematopoietic cells by: (i) providing the progenitor hematopoietic cells ex vivo with conditions for cell proliferation; (ii) providing the progenitor hematopoietic cells with an effective concentration of at least one agent capable of down-regulating activity and/or expression of a Sir2 protein and/or a down-stream effector of the Sir2 protein; thereby expanding and inhibiting differentiation of the progenitor hematopoietic cells; and (c) transplanting the progenitor hematopoietic cells into a recipient.

According to still a further aspect of the present invention there is provided a method of inhibiting maturation/differentiation of erythroid precursor cells for treatment of a subject suffering from β-hemoglobinopathic, the method comprising administering to the subject an effective concentration of at least one agent capable of down-regulating activity and/or expression of a Sir2 protein and/or a down-stream effector of the Sir2 protein, thereby expanding and inhibiting differentiation of a population of stem cells of the subject such that upon removal of agent from the subject, the stem cells undergo accelerated maturation resulting in elevated fetal hemoglobin production, thereby ameliorating symptoms of β-hemoglobinopathy in the subject.

According to still a further aspect of the present invention there is provided a method of preserving undifferentiated stem cells comprising providing the undifferentiated stem cells with an effective concentration of at least one agent capable of down-regulating activity and/or expression of a Sir2 protein and/or a down-stream effector of the Sir2 protein, wherein the providing is effected in at least one of the steps of harvesting, isolating and storage of the undifferentiated hematopoietic cells.

According to still a further aspect of the present invention there is provided stem cell collection bags, stem cell separation and stem cell washing buffers supplemented with an amount of at least one agent capable of down-regulating activity and/or expression of a Sir2 protein and/or a down-stream effector of the Sir2 protein, the amount sufficient to inhibit differentiation of a population of undifferentiated hematopoietic cells.

According to still a further aspect of the present invention there is provided sse of an agent capable of down-regulating activity and/or expression of a Sir2 protein and/or a down-stream effector of the Sir2 protein in the preparation of a medicament for expanding and inhibiting differentiation of stem cells.

According to still further features in the described preferred embodiments down-stream effector of the Sir2 protein is OAADPr.

According to still further features in the described preferred embodiments the agent capable of down-regulating Sir2 activity and/or expression is selected from the group consisting of: (i) a chemical inhibitor; (ii) an oligonucleotide inhibitor directed at a nucleic acid sequence encoding Sir2 enzyme; (iii) an antibody; and (iv) a peptide inhibitor.

According to still further features in the described preferred embodiments the chemical inhibitor is selected from the group consisting of splitomicin, sirtinol and M15.

According to still further features in the described preferred embodiments the oligonucleotide inhibitor is selected from the group consisting of an antisense, a dsRNA, a ribozyme and a DNAzyme.

According to still further features in the described preferred embodiments the antibody is selected from the group consisting of a Fab fragment, an Fv fragment, a single chain antibody and a single domain antibody.

According to still further features in the described preferred embodiments the peptide inhibitor is selected from the group consisting of a p53 derived peptide and H4 derived peptide.

According to still further features in the described preferred embodiments the Sir2 protein is selected from the group consisting of hSIRT1, hSIRT2, hSIRT3, hSIRT4, hSIRT5, hSIRT6 and hSIRT7.

The present invention successfully addresses the shortcomings of the presently known configurations by providing novel methods for differentiation-less expansion of stem cells and cells derived therefrom.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 6a shows the CD34+/CD38− population. FIG. 6b shows the CD34+/Lin− population. FIG. 6c shows the CD34+/(HLA-DR38)− populations of nicotinamide treated cells versus cytokine control cultures.

FIG. 8a is a bar graph depicting the effect of splitomicin on total cell expansion as determined by counting. FIG. 8b is a bar graph depicting the effect of splitomicin on CD34+ cell expansion as determined by both, FACS analysis and re-isolation of CD34+ cells. FIG. 8c is a bar graph depicting the effect of splitomicin on cell self-renewal potential as determined by cloning the cells in semi-solid medium and scoring colonies after 14 days.

DESCRIPTION OF THE PREFERRED EMBODIMENTS

Figure 1A:
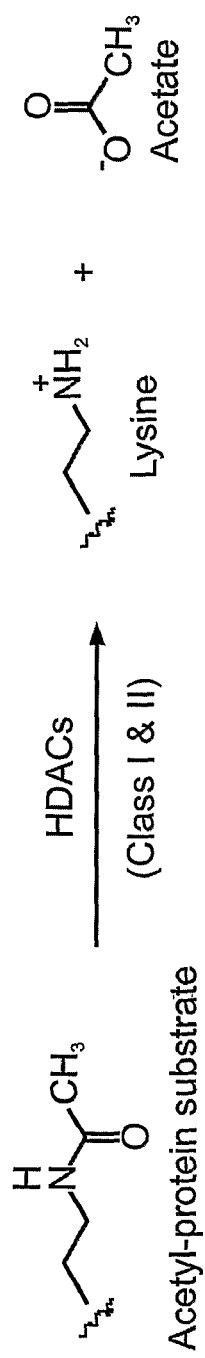
FIGS. 1a-b are prior art schemes depicting general reactions catalyzed by class I and II protein deacetylases (FIG. 1a) and class III (Sir-2) protein deacetylases [FIG. 1b, Denu (2003) TIBS 28:41-47].
Figure 1B:
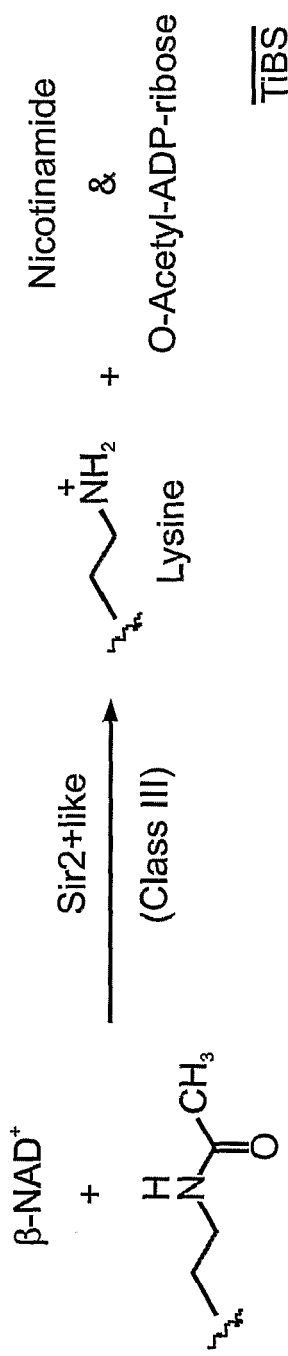

The present invention is of methods of expanding a population of stem cells, while at the same time, substantially inhibiting differentiation of the cells ex-vivo and/or in-vivo. In one embodiment, the invention facilitates the efficient use as a therapeutic ex-vivo cultured cell preparation, which includes an expanded, large population of renewable stem cells, in which differentiation was inhibited while cell expansion was propagated. Specifically in this respect, the present invention can be used to provide ex-vivo expanded populations of stem cells, which can be used for applications in hematopoietic cell transplantations, and in generation of stem cells suitable for genetic manipulations, which may be used for cellular gene therapy. Additional applications may include, but are not limited to, adoptive immunotherapy, treatments for multiple diseases, such as, for example, β-hemoglobinopathia, implantation of stem cells in an in vivo cis-differentiation and trans-differentiation settings, and ex vivo tissue engineering in cis-differentiation and trans-differentiation settings. The present invention further relates to expanded stem cell preparations and to articles-of-manufacture for preparing same.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Silent information regulator 2 (Sir2) proteins, sirtuins, are protein deacetylases dependent on nicotine adenine dinucleotide (NAD), which are found in organisms ranging from bacteria to humans. In eukaryotes, sirtuins regulate transcriptional repression, recombination, the cell-division cycle, microtubule organization, and cellular responses to DNA-damaging agents. Sirtuins have also been implicated in regulating the molecular mechanisms of aging. The Sir2 catalytic domain, which is shared among all sirtuins, consists of two distinct domains that bind NAD and the acetyl-lysine substrate. In addition to the catalytic domain, eukaryotic sirtuins contain variable amino- and carboxy-terminal extensions that regulate their subcellular localizations and catalytic activity. To date, no association has been made between Sir2 activity and stem cell differentiation.

While reducing the present invention to practice, the present inventors uncovered that culturing of hematopoietic cells with inhibitors of enzymatic reactions catalyzed by the Sir2 family of enzymes (e.g., splitomicin), results in extensive expansion of a cell population that displays phenotypic and functional characteristics of primitive hematopoietic progenitor cells.

It will be appreciated, that the present inventors have previously shown that nicotineamide, a Sir-2 inhibitor, can be used for increasing differentiation-less expansion of stem cells (see e.g., WO/03062369 to Gamida-Cell Ltd.). In this case, the activity of nictotineamide was attributed to the inhibition of CD38 and not of Sir2. Hence, the use of inhibitors for the Sir2 family of enzymes for expanding and inhibiting differentiation of stem cells presents a novel approach for stem cell ex-vivo culturing and stem cell therapy.

As is illustrated hereinbelow and in the Examples section which follows Sir2 inhibitors (i.e., nicotineamide and splitomicin) were capable of mediating preferential and substantial expansion of ex vivo cultures of late progenitor cells and stem/early progenitor cells (see Examples 1 and 2, respectively).

The newly discovered effect of inhibiting enzymatic reactions catalyzed by the Sir2 family of enzymes on stem cell differentiation/proliferation, is applicable for maximizing the ex-vivo expansion of various types of cells including hematopoietic cells, hepatocytes and embryonic stem cells. Such ex-vivo expanded cells can be applied in several clinical situations. The following lists a few.

Hematopoietic cell transplantation: Transplantation of hematopoietic cells has become the treatment of choice for a variety of inherited or malignant diseases. While early transplantation procedures utilized the entire bone marrow (BM) population, recently, more defined populations, enriched for stem cells (CD34$^+$ cells) have been used [Van Epps Blood Cells 20:411, (1994)]. In addition to the marrow, such cells could be derived from other sources such as peripheral blood (PB) and neonatal umbilical cord blood (CB) [Emerson Blood 87:3082 (1996)]. Compared to BM, transplantation with PB cells shortens the period of pancytopenia and reduces the risks of infection and bleeding [Brugger N Engl J Med 333:283, 1995; Williams Blood 87:1687, (1996); Zimmerman J Heamatotherapy 5:247, (1996)].

An additional advantage of using PB for transplantation is its accessibility. The limiting factor for PB transplantation is the low number of circulating pluripotent stem/progenitor cells.

To obtain enough PB-derived stem cells for transplantation, these cells are "harvested" by repeated leukophoresis following their mobilization from the marrow into the circulation by treatment with chemotherapy and cytokines [Brugger N Engl J Med 333:283, 1995; Williams Blood 87:1687, (1996)]. Such treatment is obviously not suitable for normal donors.

The use of ex-vivo expanded stem cells for transplantation has the following advantages [Koller Blood 82:378, (1993); Lebkowski Blood Cells 20:404, (1994)]:

It reduces the volume of blood required for reconstitution of an adult hematopoietic system and may obviate the need for mobilization and leukophoresis [Brugger N Engl J Med 333:283, 1995].

It enables storage of small number of PB or CB stem cells for potential future use.

In the case of autologous transplantation of recipients with malignancies, contaminating tumor cells in autologous infusion often contribute to the recurrence of the disease [Brugger N Engl J Med 333:283, 1995]. Selecting and expanding CD34$^+$ stem cells will reduce the load of tumor cells in the final transplant.

The cultures provide a significant depletion of T lymphocytes, which may be useful in the allogeneic transplant setting for reducing graft-versus-host disease.

Clinical studies indicate that transplantation of ex-vivo expanded cells derived from a small number of PB CD34$^+$ cells can restore hematopoiesis in recipients treated with high doses of chemotherapy, although the results do not yet allow firm conclusions about long term in-vivo hematopoietic capabilities of these cultured cells [Brugger N Engl J Med 333: 283, 1995; Williams Blood 87:1687, (1996)].

For successful transplantation, shortening of the duration of the cytopenic phase, as well as long-term engraftment, is crucial. Inclusion of intermediate and late progenitor cells in the transplant could accelerate the production of donor-derived mature cells thereby shortening the cytopenic phase. It is important, therefore, that ex-vivo expanded cells include, in addition to stem cells, more differentiated progenitor cells in order to optimize short-term recovery and long-term restoration of hematopoiesis. Expansion of intermediate and late progenitor cells, especially those committed to the neutrophilic and megakaryocytic lineages, concomitant with expansion of stem cells, should serve this purpose [Sandstrom Blood 86:958, (1995)].

Such cultures may be useful in restoring hematopoiesis in recipients with completely ablated bone marrow, as well as in providing a supportive measure for shortening recipient bone marrow recovery following conventional radio- or chemotherapies.

Prenatal diagnosis of genetic defects in scarce cells: Prenatal diagnosis involves the collection of embryonic cells from a pregnant woman, in utero, and analysis thereof for genetic defects. A preferred, non-invasive, means of collecting embryonic cells involves separation of embryonic nucleated red blood cell precursors that have infiltrated into peripheral maternal circulation. However, since the quantities of these cells are quite scarce, a further application of the present invention would be the expansion of such cells according to methods described herein, prior to analysis. The present invention, therefore, offers a means to expand embryonic cells for applications in prenatal diagnosis.

Gene therapy: For successful long-term gene therapy, a high frequency of genetically modified stem cells with transgenes stably integrated within their genome, is an obligatory requirement. In BM tissue, while the majority of cells are cycling progenitors and precursors, stem cells constitute only a small fraction of the cell population and most of them are in a quiescent, non-cycling state. Viral-based (e.g., retroviral) vectors require active cell division for integration of the transgene into the host genome. Therefore, gene transfer into fresh BM stem cells is highly inefficient. The ability to expand a purified population of stem cells and to regulate their cell division ex-vivo would provide for an increased probability of their genetic modification [Palmiter Proc Natl Acad Sci USA 91(4): 1219-1223, (1994)].

Adoptive immunotherapy: Ex-vivo-expanded, defined lymphoid subpopulations have been studied and used for adoptive immunotherapy of various malignancies, immunodeficiencies, viral and genetic diseases [Freedman Nature Medicine 2: 46, (1996); Heslop Nature Medicine 2: 551, (1996); Protti Cancer Res 56: 1210, (1996)].

The treatment enhances the required immune response or replaces deficient functions. This approach was pioneered clinically by Rosenberg et al. [Rosenberg J Natl Cancer Inst. 85: 622, 1993] using a large number of autologous ex-vivo expanded non-specific killer T cells, and subsequently ex-vivo expanded specific tumor infiltrating lymphocytes.

Functionally active, antigen-presenting cells could be grown from a starting population of CD34+ PB cells in cytokine-supported cultures, as well. These cells can present soluble protein antigens to autologous T cells in-vitro and, thus, offer new prospects for the immunotherapy of minimal residual disease after high dose chemotherapy. Ex-vivo expansion of antigen-presenting dendritic cells has been studied as well, and is an additional promising application of the currently proposed technology [Bernhard Cancer Res 10: 99, (1995); Fisch Eur J Immunol 26: 595, (1996); Siena Expt Hematol 23:1463, (1996)].

Ex-Vivo Expansion of Non-Hematopoietic Stem and Progenitor Cells:

Additional applications of the technology proposed herein include the possibility for ex-vivo expansion of non-hematopoietic stem and progenitor cells, including, for example, neural stem cells, oligodendrocyte progenitors, and the like.

Myelin disorders form an important group of human neurological diseases that are, as yet, incurable. Progress in animal models, particularly in transplanting cells of the oligodendrocyte lineage, has resulted in significant focal remyelination and physiological evidence of restoration of function [Repair of myelin disease: Strategies and progress in animal models. Molecular Medicine Today. December 1997. pp. 554-561]. Future therapies could involve both transplantation and promotion of endogenous repair, and the two approaches could be combined with ex-vivo manipulation of donor tissue.

U.S. Pat. No. 5,486,359 illustrates that isolated human mesenchymal stem cells can differentiate into more than one tissue type (e.g. bone, cartilage, muscle, or marrow stroma) and provides a method for isolating, purifying, and expanding human mesenchymal stem cells in culture.

U.S. Pat. No. 5,736,396 provides methods for in-vitro or ex-vivo lineage-directed induction of isolated, culture-expanded human mesenchymal stem cells comprising mesenchymal stem cell contact with a bioactive factor effective in inducing stem cell differentiation into a lineage of choice. Further disclosed is a method including introducing culture-expanded lineage-induced mesenchymal stem cells into the original, autologous host, for purposes of mesenchymal tissue regeneration or repair.

U.S. Pat. No. 4,642,120 provides compositions for repairing defects in cartilage and bones. These are provided in gel form either as such, or embedded in natural or artificial bones. The gel comprises certain types of cells. Cells may be committed embryonal chondrocytes or any mesenchymal-origin cells which potentially can be converted to become functional cartilage cells, typically by the inclusion of chondrogenic inducing factors, in combination with fibrinogen, antiprotease and thrombin.

U.S. Pat. No. 5,654,186 illustrates that blood-borne mesenchymal cells proliferate in culture, and in-vivo, as demonstrated in animal models, and are capable of migrating into wound sites from the blood to form skin.

U.S. Pat. No. 5,716,411 reveals a method of skin regeneration of a wound or burn in an animal or human. This method comprises the steps of initially covering the wound with a collagen glycosaminoglycan (GC) matrix, facilitating mesenchymal cell and blood vessel infiltration from healthy underlying tissue within the grafted GC matrix. Subsequently a cultured epithelial autograft sheet grown from epidermal cells taken from the animal or human at a wound-free site is applied on the body surface. The resulting graft has excellent inclusion rates and has the appearance, growth, maturation and differentiation of normal skin.

U.S. Pat. No. 5,716,616 provides methods for treating recipients suffering from diseases, disorders or conditions characterized by bone, cartilage, or lung defects. The methods comprise intravenous administration of stromal cells isolated from normal, syngeneic individuals, or intravenous administration of stromal cells isolated from the recipient subsequent to correction of the genetic defect in the isolated cells. Methods of introducing genes into a recipient individual are also disclosed. The methods comprise obtaining a bone marrow sample from either the recipient individual or a matched syngeneic donor and isolating adherent cells from the sample. Once isolated, donor adherent cells are transfected with a gene and administered to a recipient individual intravenously. Compositions comprising isolated stromal cells that include exogenous genes operably linked to regulatory sequences are disclosed, as well.

In each of the above examples, non-hematopoietic stem and progenitor cells are used as an external source of cells for replenishing missing or damaged cells of an organ. Such use requires high levels of stem and progenitor cell expansion for successful application of the proposed therapies. Because of this pressing need for large numbers of expanded stem and progenitor cell populations, the methods and applications of the present invention address a critical niche in any of the methods disclosed in the above U.S. patents.

Additional Examples for Both Ex-Vivo and In-Vivo Applications:

Additional applications of stem and progenitor cell expansion include skin regeneration, hepatic regeneration, muscle regeneration and stimulation of bone growth for applications in osteoporosis.

Mobilization of bone marrow stem cells into peripheral blood (peripheralization): Effects of down regulating SIR activity and/or expression have additional in-vivo applications. As mentioned above, PB-derived stem cells for transplantation are "harvested" by repeated leukophoresis following their mobilization from the marrow into the circulation by treatment with chemotherapy and cytokines [Brugger N Engl J Med 333:283, (1995); Williams Blood 87:1687, (1996)].

The use of chemotherapy is, of course, not suitable for normal donors. Administration of antagonists, into the donor could increase the marrow stem cell pool which is then mobilized into the periphery by endogenous or injected G-CSF.

Stimulation of fetal hemoglobin production: Increased fetal hemoglobin has been shown to ameliorate clinical symptoms in recipients suffering β-hemoglobinopathies, such as sickle cell anemia and β-thalassemia [Schechtez A N et al. Sickle cell anemia. In: Molecular basis of blood diseases. Stamatoyannaopoulos G, Nienhuis A W, Leder P and Majerus P W Eds. pp. 179-218, Sounders Philadelphia].

Fetal hemoglobin, which normally comprises 1% of the total hemoglobin, becomes elevated in accelerated erythropoiesis [e.g., following acute hemolysis or hemorrhage or administration of erythropoietin, Alter Experimental Hematology 7: 200, (1979)].

It has been suggested that this phenomenon is associated with acceleration of the maturation/differentiation process of erythroid precursors [Blau Blood 81: 227, (1993)]. Administration of modulators of SIR proteins activity or expression to recipients with β-hemoglobinopathies might first increase and synchronize their early erythroid progenitor pool, by blocking progenitor differentiation.

Following cessation of administration of the drug and its removal from the body, this early population then might undergo accelerated maturation, which may result in an elevated production of fetal hemoglobin.

The following description provides more details relating to specific aspects and embodiments of the present invention.

Thus, according to one aspect of the present invention there is provided a method of expanding and inhibiting differentiation of a population of stem cells, the method comprising providing the stem cells with an agent capable of down-regulating activity and/or expression of a SIR protein and/or a down-stream effector of said SIR protein, thereby expanding and inhibiting differentiation of the population of stem cells.

As used herein the phrase "Sir2 protein" refers to at least one enzyme of the Sir2 family of deacetylases. Sir2 protein of the present invention is preferably a eukaryotic Sir2 protein, more preferably a mammalian Sir2 protein (e.g., mouse, primate, human), most preferably a human Sir2 protein. Examples of human Sir2 proteins include, but are not limited to, SIRT1 (GenBank Accession No. NP_036370), SIRT2 (GenBank Accession No. NP_085096), SIRT3 (GenBank Accession No. NP_036371), SIRT4 (GenBank Accession No. NP_036372), SIRT5 (GenBank Accession No. NP_112534), SIRT6 (GenBank Accession No. NM_057623) and SIRT7 (GenBank Accession No. NM_057622).

As used herein the phrase "down-stream effector of a Sir2 protein" refers to a reaction product of a Sir2 catalysis. An example of a down-stream effector of a Sir2 protein is O-acetyl-ADP-ribose (OAADPr) which is generated by the transfer of the acetyl group (removed from the Sir2 substrate) to the ADP-ribose. OAADPr is thought to act as a second messenger (see Background section).

As used herein the phrase "Sir2 activity" refers to the catalytic activity of Sir2 family of protein deacetylases, essentially hydrolysis of one molecule of NAD+ for each molecule of acetylated lysine, becoming deacetylated, and the production of one molecule of deacetylated lysine, nicotineamide and OAADPr. Other catalytic reactions catalyzed by this family of enzymes are also envisaged by the present invention, such as ribosyl-transferase (SIRT6). The phrase Sir2 activity as used herein, also refers to a biological function regulated by Sir2 family of proteins, such as for example, gene silencing, chromosome stability or cell survival (apoptosis) transcription factor regulation.

As used herein the phrase "Sir2 expression" refers to expression at the protein level and/or at the mRNA level. Generally, the level of expression is affected by the balance between protein synthesis and protein degradation (a similar balance exists also at the mRNA level).

As used herein the term "inhibiting" refers to slowing, decreasing, delaying, preventing, reversing or abolishing. Similarly, the term "downregulation" refers to reducing, partially or totally, the indicated activity or expression.

As used herein the term "differentiation" refers to relatively generalized or specialized changes during development. Cell differentiation of various lineages is a well-documented process and requires no further description herein. As used herein the term differentiation is distinct from maturation which is a process, although sometimes associated with cell division, in which a specific cell type mature to function and then dies, e.g., via programmed cell death.

The phrase "cell expansion" is used herein to describe a process of cell proliferation substantially devoid of cell differentiation. Cells that undergo expansion hence maintain their cell renewal properties and are oftentimes referred to herein as renewable cells, e.g., renewable stem cells.

As used herein, the phrase "stem cells" refers to pluripotent cells that, given the right growth conditions, can develop to any cell lineage present in the organism from which they were derived. The phrase, as used herein, refers both to the earliest renewable cell population responsible for generating cell mass in a tissue or body and the very early progenitor cells, which are somewhat more differentiated, yet are not committed and can readily revert to become a part of the earliest renewable cell population. The stem cells used for cell expansion in context of the present invention can be obtained from any tissue of any multicellular organism including both animals and plants. Stem cells were shown to exist in many organs and tissues and are believed to exist in all tissues of animals, including, but not limited to, bone marrow (Rowley S D et al. (1998) Bone Marrow Transplant 21: 1253), peripheral blood (Koizumi K, (2000) Bone Marrow Transplant 26: 787, liver (Petersen B E et al. (1998) Hepatology 27: 433) and brain (Pagano S F et al. (2000) Stem Cells 18: 295). It is anticipated that all such cells are expandable using the methods of the present invention.

Methods of ex-vivo culturing stem cells of different tissue origins are well known in the art of cell culturing. To this effect, see for example, the text book "Culture of Animal Cells—A Manual of Basic Technique" by Freshney, Wiley-Liss, N.Y. (1994), Third Edition, the teachings of which are hereby incorporated by reference.

As used herein the phrase "population of stem cells" refers to a subset of stem cells characterized by a desired feature (e.g., responsiveness to Sir2 down-regulation, as described herein). It is well established that stem cell populations are of a heterogeneous nature in terms of pluripotency, differentiation marker expression and the like. The population of stem cells of this aspect of the present invention may be comprised in a mixed cell population, which comprises committed cells as well, which may be distinguished from the stem cells in terms of self-renewal, surface marker expression, ability to form colonies in soft agar and the like (see Examples section).

One most surprising result obtained while reducing the present invention to practice was that stem cells present in the mononuclear cell fraction of cord blood (i.e., mixed population), can undergo expansion using the methods of the present invention. Hence, according to an embodiment of the present invention, the stem cells that undergo expansion are mixed (e.g., not separated from, not enriched) with committed cells. This embodiment of the present invention is of particular advantage because it relieves the tedious need for cell separation prior to ex-vivo culturing the cells.

In another embodiment, the cells are enriched for hematopoietic CD133+ cells or CD34$^+$ cells and are characterized by an absence, or significantly diminished expression of cell surface antigens CD38 and Lineage specific antigens (Lin, including: CD3, CD61, CD19, CD33, CD14, CD15 and/or CD4).

Stem cells of this aspect of the present invention can be embryonic stem cells or adult stem cells. Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). Adult stem cells are stem cells, which are derived from tissues of adults and are also well known in the art. Methods of isolating or enriching for adult stem cells are described in, for example, Miraglia, S. et al. (1997) Blood 90: 5013, Uchida, N. et al. (2000) Proc. Natl. Acad. Sci. USA 97: 14720, Simmons, P. J. et al. (1991) Blood 78: 55, Prockop D J (Cytotherapy (2001) 3: 393), Bohmer R M (Fetal Diagn Ther (2002) 17: 83) and Rowley S D et al. (Bone Marrow Transplant (1998) 21: 1253), Stem Cell Biology Daniel R. Marshak (Editor) Richard L. Gardner (Editor), Publisher: Cold Spring Harbor Laboratory Press, (2001) and Hematopoietic Stem Cell Transplantation. Anthony D. Ho (Editor) Richard Champlin (Editor), Publisher: Marcel Dekker (2000).

Stem cells of the present invention may be derived from any source which comprises such cells. Examples include, but are not limited to, hematopoietic cells, neural cells, oligodendrocyte cells, skin cells, hepatic cells, embryonal stem cells, muscle cells bone cells, pancreatic cells, chondrocytes and stroma cells.

A presently preferred source for adult stem cells is the hematopoietic system including early hematopoietic cells and/or hematopoietic stem cells (as described hereinabove. Hence, according to a preferred embodiment of the present invention the stem cells are hematopoietic stem cells. Such stem cells can be derived from bone marrow, peripheral blood and neonatal umbilical cord blood. Methods of enriching white blood cells (mononuclear cells) for stem cells are well known in the art, including, selecting for CD133 and $CD34^+$ expressing cells. CD $133^+$ and $CD34^+$ cells include pluripotent stem cells and very early progenitor cells, which, under the appropriate conditions may revert to stem cells, as they are not committed cells.

According to a particular embodiment of this aspect of the present invention expanding and inhibiting differentiation of the above-mentioned stem cells is effected ex-vivo.

As used herein the term "ex-vivo" refers to a process in which cells are removed from a living organism and are propagated outside the organism (e.g., in a test tube). As used herein, the term "ex-vivo", however, does not refer to a process by which cells known to propagate only in-vitro, such as various cell lines (e.g., HL-60, MEL, HeLa, etc.) are cultured. Such cells proliferate spontaneously in culture, without differentiation, in the absence of cytokines or specific differentiation-inhibiting factors, and are "committed" (differentiated), and not undifferentiated stem or progenitor cells, as taught and claimed for the present invention. Such cell lines are, by definition, "blocked" in their ability to undergo spontaneous differentiation, and as such cannot constitute a model for demonstrating effects of Sir2 enzymes on hematopoietic stem cells and/or progenitor cells. In other words, cells expanded ex-vivo according to the present invention do not transform into cell lines in that they eventually undergo differentiation.

ex-vivo expansion of stem cells while inhibiting inhibition can be effected, according to this aspect of the present invention, by providing the stem cells ex vivo with conditions for cell proliferation; and ex vivo expanding the stem cells with said agent, thereby ex vivo expanding and inhibiting differentiation of the population of stem cells.

As used herein "conditions for cell proliferation" include the chemical and physical conditions (e.g., temperature) which are required for cell proliferation. Examples of chemical conditions which may support cell proliferation, include but are not limited to buffers, nutrients as well as cytokines which are typically provided in the growth (i.e., culture) medium.

According to preferred embodiments of the present invention, providing the stem cells with the conditions for ex-vivo cell proliferation comprises providing the cells with nutrients and with cytokines. Preferably, the cytokines are early acting cytokines, such as, but not limited to, stem cell factor, FLT3 ligand, interleukin-1, interleukin-2, interleukin-3, interleukin-6, interleukin-10, interleukin-12, tumor necrosis factor-α and thrombopoietin. It will be appreciated in this respect that novel cytokines are continuously discovered, some of which may find uses in the methods of cell expansion of the present invention.

Late acting cytokines can also be used. These include, for example, granulocyte colony stimulating factor, granulocyte/macrophage colony stimulating factor, erythropoietin, FGF, EGF, NGF, VEGF, LIF, Hepatocyte Growth Factor and macrophage colony stimulating factor.

Figure 9A:
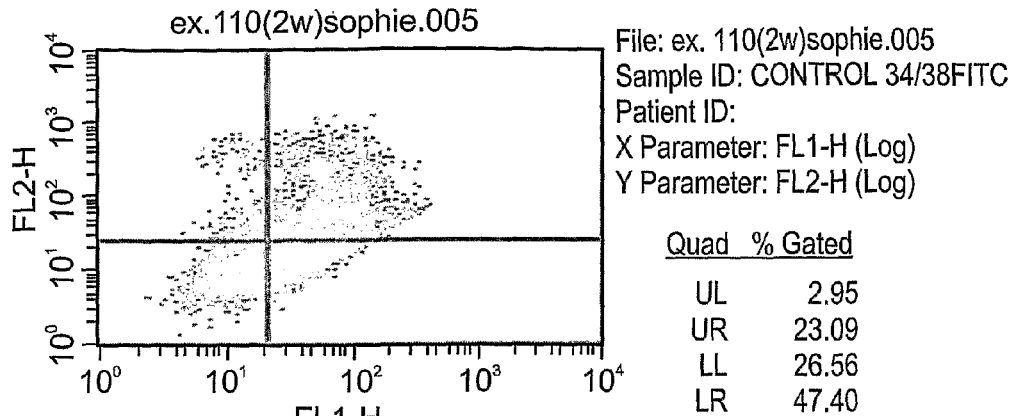
FIGS. 9a-c are dot plots presenting FACS analyses showing stem-cell cell population distribution in the absence (FIG. 9a) or presence (FIG. 9b 50 mM, FIG. 9c, 75 mM) of splitomicin. The CD34+/CD38− population is shown in the upper left part of each plot. Note, the remarkable up-left shift in the presence of 75 mM splitomicin.
Figure 9B:
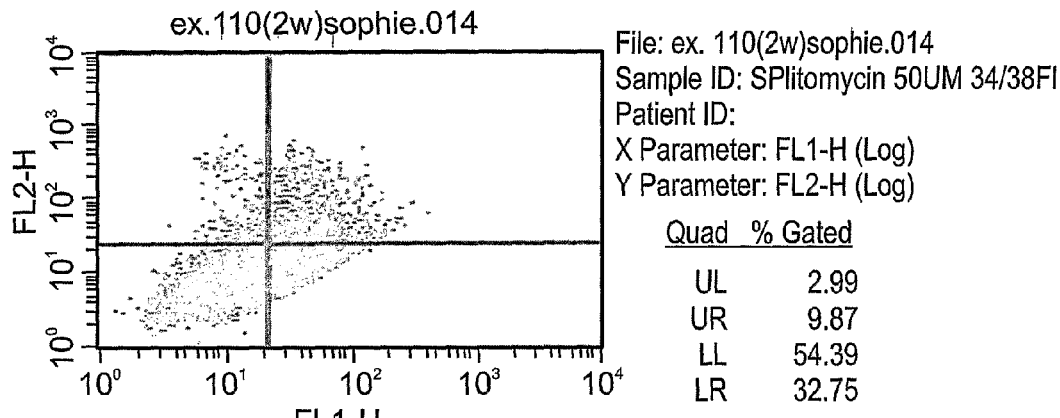
Figure 9C:
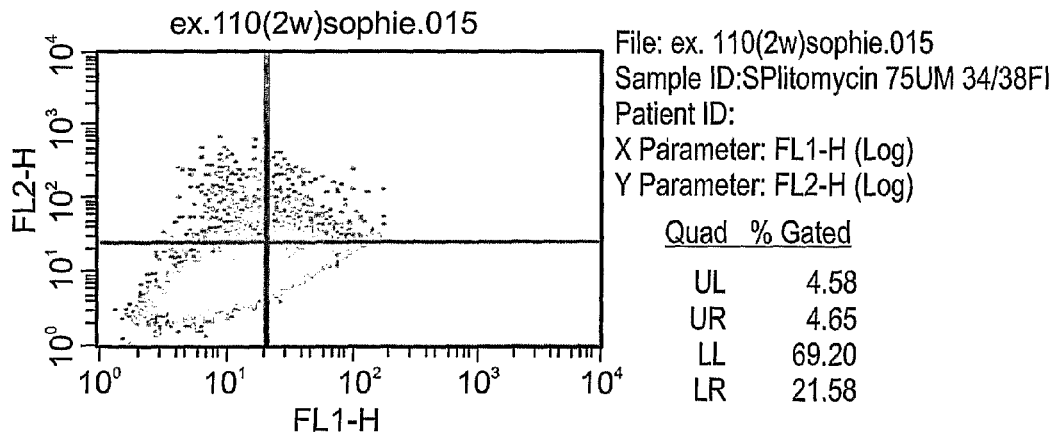

As mentioned hereinabove, concomitant with treating the cells with conditions which allow for ex-vivo the stem cells to proliferate, the cells are short-term treated or long-term treated to reduce the expression and/or activity of Sir2 proteins or down-stream effectors thereof. For example, the cultures are treated for up to 3-weeks. As is shown in Example 1 of the Examples section which follows (see FIGS. 6a-c), evaluation of culture performance at the termination of the treatment phase (nicotineamide, a Sir2 inhibitor) demonstrates higher percentages of early progenitor cells (CD34+ CD38− cells) in treated than in control cultures (cytokine treated cells). These results were further supported by another inhibitor of the Sir2 activity, splitomicin, which enhanced the differentiation-less expansion of CD34+CD38− cells (FIGS. 9a-c).

Figure 8A:
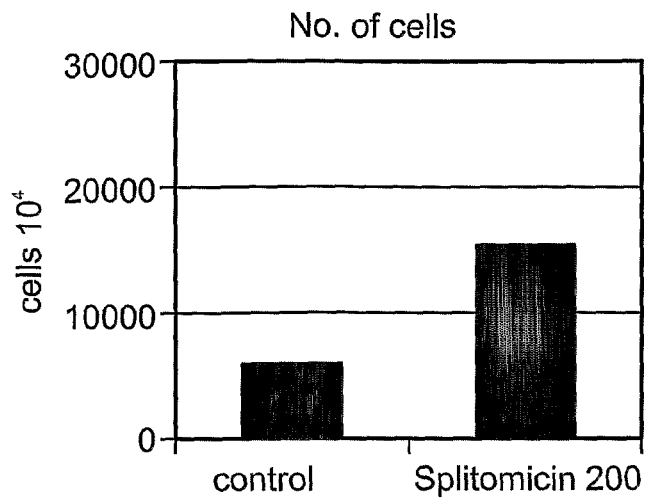
FIGS. 8a-c are bar graphs depicting the effect of splitomicin on CD34+ cell expansion.
Figure 8B:
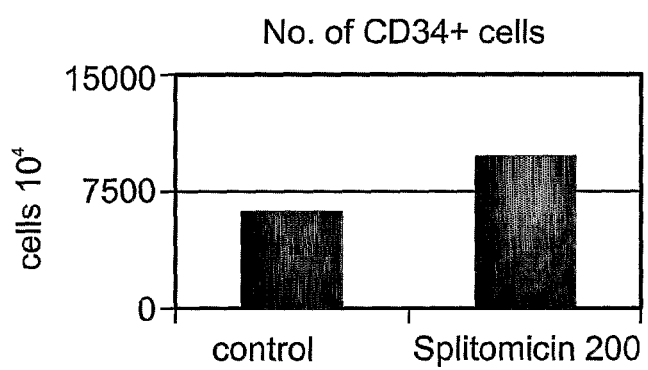
Figure 8C:
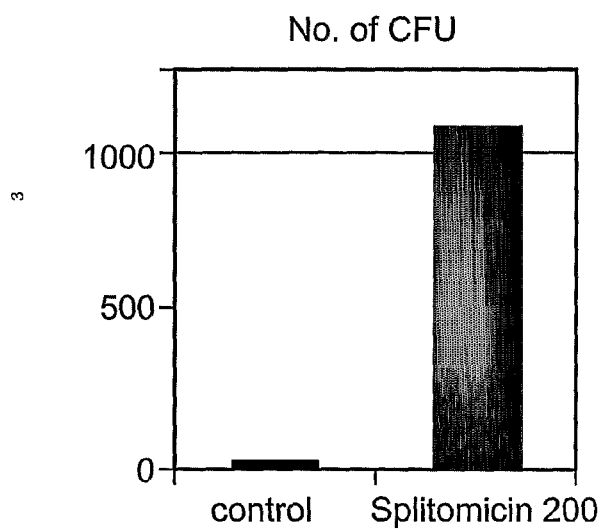

In the long-term assay phase (see Example 2 of the Examples section which follows), cultures pre-treated with Splitomicin demonstrate remarkable expansion of total nuclear cells and progenitor cells (CD34+ and CFUc, FIGS. 8b-c, respectively).

Agents capable of down-regulating expression and/or activity of Sir2 proteins or down-stream effectors thereof include, but are not limited to, chemical inhibitors; oligonucleotide inhibitors directed at a nucleic acid sequence encoding Sir2 protein; and protein inhibitors, such as antibodies specifically recognizing a Sir2 protein; and peptide inhibitors.

The following describes specific agents which may be used in accordance with the present invention.

Chemical inhibitors—Numerous protein deacetylase inhibitors are known in the art, with varying affinities towards Sir2-like proteins. Examples of such inhibitors are listed in U.S. Pat. Appl. No. 20040142859. Preferably used in accordance with the present invention, are Sir2 specific inhibitors. A number of Sir2 chemical inhibitors are known in the art. Examples include, but are not limited to, sirtinol and vitamin B3 [Luo, et al. (2001) Cell 107:137-148], splitomicin [Bedalov, et al. (2001) Proc. Natl. Acad. Sci. 98, 15113-15118] and M15 [Bitterman (2002) J. Biol. Chem. 277:45099-107]. These chemical inhibitors are commercially available from various vendors, such as from Sigma (St. Louis, USA), Chembridge (San Diego, Calif., USA).

Sir2 phosphorylation is highly correlated with an active form thereof [Dryden (2003) Mol. Cell. Biol. 23:3173-85]. These findings suggest that protein de-phosphorylation may be effective in down-regulating Sir2 activity. This may be achieved by phosphorylation (i.e., kinase) inhibitors, which are well known in the art. Alternatively, overexpression of phosphatases such as CDC14B may result in dephosphorylation of Sir2 proteins as has been shown by Dryden et al. Supra, and further described hereinbelow.

Active derivatives of the inhibitors described herein are also envisaged by the present invention. Such derivatives may be qualified using the biochemical assays for Sir2 activity, further described hereinbelow, or by testing the effect thereof on stem cell differentiation.

Oligonucleotide inhibitors—Down-regulation of Sir2 protein expression can be effected using oligonucleotide molecules designed to specifically block the transcription of Sir2 mRNA, or the translation of Sir2 transcripts at the ribosome.

The term "oligonucleotide" refers to a single-stranded or double-stranded oligomer or polymer of ribonucleic acid (RNA) or deoxyribonucleic acid (DNA) or mimetics thereof. This term includes oligonucleotides composed of naturally occurring bases, sugars, and covalent internucleoside linkages (e.g., backbone), as well as oligonucleotides having non-naturally occurring portions, which function similarly to respective naturally occurring portions.

Oligonucleotides designed according to the teachings of the present invention can be generated according to any oligonucleotide synthesis method known in the art, such as enzymatic synthesis or solid-phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

The oligonucleotide of the present invention is of at least 17, at least 18, at least 19, at least 20, at least 22, at least 25, at least 30 or at least 40, bases specifically hybridizable with sequence alterations described hereinabove.

The oligonucleotides of the present invention may comprise heterocylic nucleosides consisting of purines and the pyrimidines bases, bonded in a 3'-to-5' phosphodiester linkage.

Preferably used oligonucleotides are those modified either in backbone, internucleoside linkages, or bases, as is broadly described hereinunder.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

In one embodiment, oligonucleotides agents of the present invention are antisense oligonucleotides.

Design of antisense molecules which can be used to efficiently inhibit Sir2 protein expression must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof. Sequences suitable for use in construction and synthesis of oligonucleotides which specifically bind to Sir2 mRNA, genomic DNA, promoter and/or other control sequences of Sir2 are available in published Sir2 nucleotide sequences, including, but not limited to, GenBank Accession Nos: SIRT1 (GenBank Accession No. NM_012238), SIRT2 (GenBank Accession No. NM_012237), SIRT3 (GenBank Accession No. NM_012239), SIRT4 (GenBank Accession No. NM_012240), SIRT5 (GenBank Accession No. NM_012241), SIRT6 (GenBank Accession No. NM_016539) and SIRT7 (GenBank Accession No. NM_016538).

The prior art teaches of a number of delivery strategies which can be used to efficiently deliver oligonucleotides into a wide variety of cell types (see, for example, Luft (1998) J Mol Med 76(2): 75-6; Kronenwett et al. (1998) Blood 91(3): 852-62; Rajur et al. (1997) Bioconjug Chem 8(6): 935-40; Lavigne et al. (1997) Biochem Biophys Res Commun 237(3): 566-71 and Aoki et al. (1997) Biochem Biophys Res Commun 231(3): 540-5).

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. (1999) Biotechnol Bioeng 65(1): 1-9].

Such algorithms have been successfully employed to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al. (1998) *Nature Biotechnology* 16, 1374-1375).

Several clinical trials have demonstrated safety, feasibility and activity of antisense oligonucleotides. For example, antisense oligonucleotides suitable for the treatment of cancer have been successfully used (Holmund et al. (1999) Curr Opin Mol Ther 1(3):372-85), while treatment of hematological malignancies via antisense oligonucleotides targeting c-myb gene, p53 and Bcl-2 had entered clinical trials and had been shown to be tolerated by patients [Gerwitz (1999) Curr Opin Mol Ther 1(3):297-306].

More recently, antisense-mediated suppression of human heparanase gene expression has been reported to inhibit pleural dissemination of human cancer cells in a mouse model [Uno et al. (2001) Cancer Res 61(21):7855-60].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another oligonucleotide agent capable of downregulating Sir2 expression is a small interfering RNA (siRNA) molecule in the process of RNA interference (RNAi). RNAi is a two-step process. In the first, the initiation step, input double-stranded (dsRNA) is digested into 21- to 23-nucleotide (nt) small interfering RNAs (siRNAs), probably by the action of Dicer, a member of the RNase III family of dsRNA-specific ribonucleases, which processes (cleaves) dsRNA (introduced directly or by means of a transgene or a virus) in an ATP-dependent manner. Successive cleavage events degrade the RNA to 19- to 21-bp duplexes (the siRNA), each with 2-nucleotide 3' overhangs (Hutvagner, G. and Zamore. P. D. (2002). RNAi: Nature abhors a double-strand. Curr Opin Gen Dev 12, 225-232; and Bernstein, E. (2001). Role for a bidentate ribonuclease in the initiation step of RNA interference. Nature 409, 363-366).

In the second step, termed the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base-pairing interactions and cleaves the mRNA into 12-nucleotide fragments from the 3' terminus of the siRNA (Hutvagner and Zamore (2002); Hammond et al. (2001) Nat. Rev. Gen. 2:110-119 (2001); and Sharp, P. A. (2001). RNA interference. Genes Dev 15, 485-490). Although the mechanism of cleavage remains to be elucidated, research indicates that each RISC contains a single siRNA and an RNase (Hutvagner and Zamore (2002)).

Because of the remarkable potency of RNAi, an amplification step within the RNAi pathway has been suggested. Amplification could occur by copying of the input dsRNAs to generate more siRNAs, or by replication of the siRNAs formed. Alternatively or additionally, amplification could be effected by multiple turnover events of the RISC (Hammond et al. (2001), Sharp (2001); and Hutvagner and Zamore (2002)). For more information on RNAi, see the following reviews: Tuschl, T. (2001). RNA interference and small interfering RNAs. ChemBioChem 2, 239-245; Cullen, B. R. (2002). RNA interference: antiviral defense and genetic tool. Nat Immunol 3, 597-599; and Brantl, S. (2002). Antisense-RNA regulation and RNA interference. Biochim Biophys Acta 1575, 15-25.

Synthesis of RNAi molecules suitable for use with the present invention can be effected as follows. First, the Sir2 mRNA sequence is scanned downstream of the AUG start codon for AA-dinucleotide sequences. Occurrence of each AA and the 19 3'-adjacent nucleotides is recorded as a potential siRNA target site. Preferably, siRNA target sites are selected from the open reading frame (ORF), as untranslated regions (UTRs) are richer in regulatory protein binding sites. UTR-binding proteins and/or translation initiation complexes may interfere with binding of the siRNA endonuclease complex (Tuschl (2001)). It will be appreciated, however, that siRNAs directed at untranslated regions may also be effective, as demonstrated for GAPDH, wherein siRNA directed at the 5' UTR mediated about a 90% decrease in cellular GAPDH mRNA and completely abolished protein levels (www.ambion.com/techlib/tn/91/912.html).

Second, potential target sites are compared to an appropriate genomic database (e.g., human, mouse, rat, etc.) using any sequence alignment software, such as the BlastN software available from the NCBI server (www.ncbi.nlm.nih.gov/BLAST/). Putative target sites that exhibit significant homology to other coding sequences are filtered out.

Qualifying target sequences are selected as templates for siRNA synthesis. Preferred sequences are those including low G/C content, as these have proven to be more effective in mediating gene silencing as compared with sequences including G/C content higher than 55%. Several target sites are preferably selected along the length of the target gene for evaluation. For better evaluation of the selected siRNAs, a negative control is preferably used in conjunction. Negative-control siRNAs preferably include the same nucleotide composition as the siRNAs but lack significant homology to the genome. Thus, a scrambled nucleotide sequence of the siRNA is preferably used, provided it does not display any significant homology to any other gene.

Examples of siRNA molecules which have been demonstrated capable of down-regulating the expression of Sir2 are the SIRT1 specific siRNA oligonucleotides described by Picard (2004) Nature, 429:771-6, incorporated herein by reference. SIRT2 specific siRNA molecules are described by Hamilton (2005) Genes Dev. 19:1544-55, incorporated herein by reference.

Other examples for siRNA molecules which can be used in accordance with the present invention are provided in Table 1, below.

TABLE 1

|       | siRNA target sequence   | Seq id no: | Score | Region | Start | GC Content | 1 | 2 | 3 | 4 | 5 | 6 | 7 | 8 |
|-------|-------------------------|------------|-------|--------|-------|------------|---|---|---|---|---|---|---|---|
| sirt1 | GAAGTGCCTCAGATATTAA     | 1          | 9     | ORF    | 1425  | 36.84%     | + | + | + | + |   |   | + | + |
|       | ACACTGTGGCAGATTGTTA     | 2          | 8     | ORF    | 708   | 42.11%     | + | + | + | + |   |   | + | + |
|       | TAATATCCTTTCAGAACCA     | 3          | 8     | ORF    | 728   | 31.58%     | + | + | + | + | + | + | + | + |
|       | AAGCGATGTTTGATATTGA     | 4          | 8     | ORF    | 934   | 31.58%     | + | + | + | + |   | + | + | + |
|       | AGCGATGTTTGATATTGAA     | 5          | 8     | ORF    | 935   | 31.58%     | + | + | + | + |   | + | + | + |
|       | TAAGACCAGTAGCACTAAT     | 6          | 8     | ORF    | 1387  | 36.84%     | + | + | + |   | + | + | + | + |
|       | TCTGTTCGGTGATGAAATT     | 7          | 8     | ORF    | 491   | 36.84%     | + | + | + |   |   | + | + | + |
|       | TCCTCGAACAATTCTTAAA     | 8          | 8     | ORF    | 644   | 31.58%     | + | + | + | + |   |   | + | + |
|       | TAGGTTAGGTGGTGAATAT     | 9          | 8     | ORF    | 1526  | 36.84%     | + | + | + |   |   | + | + | + |
| sirt2 | GAAGCCTGATATCGTCTTT     | 10         | 8     | ORF    | 884   | 42.11%     | + | + | + |   | + | + | + | + |
|       | CCAGAGGCCATCTTTGAGA     | 11         | 7     | ORF    | 543   | 52.63%     | + | + | + | + | + |   | + | + |
|       | GATCAGCTATTTCAAGAAA     | 12         | 7     | ORF    | 560   | 31.58%     | + | + |   | + |   | + | + | + |
|       | GCTACACGCAGAACATAGA     | 13         | 7     | ORF    | 691   | 47.37%     | + | + | + | + |   |   | + | + |
|       | CCTCGCCAAGGAACTCTAT     | 14         | 6     | ORF    | 599   | 52.63%     | + | + | + |   |   |   | + | + |
|       | GTCGCAGAGTCATCTGTTT     | 15         | 6     | ORF    | 427   | 47.37%     | + | + |   |   |   | + | + | + |
|       | CGGCACCTTCTACACATCA     | 16         | 6     | ORF    | 761   | 52.63%     | + | + | + | + |   |   | + | + |
|       | ACATGGACTTCCTGCGGAA     | 17         | 6     | ORF    | 310   | 52.63%     | + |   |   | + | + | + | + | + |
| sirt3 | CAACGTCACTCACTACTTT     | 18         | 8     | ORF    | 651   | 42.11%     | + | + | + |   | + | + | + | + |
|       | CCAACGTCACTCACTACTT     | 19         | 7     | ORF    | 650   | 47.37%     | + | + | + |   | + |   | + | + |
|       | TTCGAGTATTAAAGGTGGA     | 20         | 6     | ORF    | 309   | 36.84%     | + |   | + | + |   | + | + | + |
|       | ACGTCACTCACTACTTTCT     | 21         | 6     | ORF    | 653   | 42.11%     | + | + | + |   |   |   | + | + |
|       | ACCTGCACAGTCTGCCAAA     | 22         | 6     | ORF    | 796   | 52.63%     | + | + | + | + |   |   | + | + |
| sirt4 | TGAGCTTTGCGTTGACTTT     | 23         | 7     | ORF    | 28    | 42.11%     | + | + | + |   | + |   | + | + |
|       | AAAGGCCGTTGGATCGCAA     | 24         | 7     | ORF    | 57    | 52.63%     | + |   | + | + | + | + | + | + |
|       | AAGATGAGCTTTGCGTTGA     | 25         | 6     | ORF    | 24    | 42.11%     | + | + | + | + |   | + | + | + |
|       | AGATGAGCTTTGCGTTGAC     | 26         | 6     | ORF    | 25    | 47.37%     | + | + | + |   | + | + |   | + |
|       | GAGTTACAGCGCTTCATCA     | 27         | 6     | ORF    | 156   | 47.37%     | + | + | + |   |   | + | + | + |

TABLE 1-continued

| | siRNA target sequence | Seq id no: | Score | Region | Start | GC Content | 1 | 2 | 3 | 4 | 5 | 6 | 7 | 8 |
|---|---|---|---|---|---|---|---|---|---|---|---|---|---|---|
| | TTCGTAGGCTGGCCTCAAT | 28 | 6 | ORF | 348 | 52.63% | + | + |   |   |   | + | + | + |
| | TCGGAAAGCTGTACTGGTT | 29 | 6 | ORF | 421 | 47.37% | + | + | + |   |   | + | + | + |
| | GCAAGAGCGTTTCCAAGTC | 30 | 6 | ORF | 563 | 52.63% | + | + | + |   | + | + |   | + |
| sirt5 | GATCCATGGTAGCTTATTT | 31 | 8 | ORF | 764 | 36.84% | + | + | + |   |   | + | + | + |
| | ATCCATGGTAGCTTATTTA | 32 | 8 | ORF | 765 | 31.58% | + | + | + | + |   |   | + | + |
| | TCCATGGTAGCTTATTTAA | 33 | 8 | ORF | 766 | 31.58% | + | + | + | + |   |   | + | + |
| | AAAGTGGTGTTCCGACCTT | 34 | 7 | ORF | 487 | 47.37% | + | + | + |   | + | + | + | + |
| | AGATCCATGTGTAGCTTATT | 35 | 7 | ORF | 763 | 36.84% | + | + | + |   | + |   | + |   |
| | GTTCAAGTATGGCAGATTT | 36 | 7 | ORF | 406 | 36.84% | + | + | + |   |   | + | + | + |
| | AGCTGGTGTTAGTGCAGAA | 37 | 7 | ORF | 470 | 47.37% | + | + | + | + |   | + | + | + |
| | TGGTGTTCCGACCTTCAGA | 38 | 6 | ORF | 491 | 52.63% | + | + | + | + |   |   | + | + |
| | AGTGGTGTTCCGACCTTCA | 39 | 6 | ORF | 489 | 52.63% | + | + | + | + |   |   | + | + |
| | GCTGGTGTTAGTGCAGAAA | 40 | 6 | ORF | 471 | 47.37% | + | + | + | + |   |   | + |   |
| sirt6 | GGAAGAATGTGCCAAGTGT | 41 | 7 | ORF | 474 | 47.37% | + | + | + |   | + | + | + | + |
| | CCAAGTGTAAGACGCAGTA | 42 | 7 | ORF | 485 | 47.37% | + | + | + | + | + |   | + | + |
| | GCATCCATGGCTACGTTGA | 43 | 7 | ORF | 818 | 52.63% | + | + | + | + | + |   | + | + |
| | TAAGACGCAGTACGTCCGA | 44 | 5 | ORF | 492 | 52.63% | + |   |   | + | + |   | + | + |
| | GTGCCAAGTGTAAGACGCA | 45 | 5 | ORF | 482 | 52.63% | + |   | + | + |   |   | + | + |
| | TCCATGGCTACGTTGACGA | 46 | 5 | ORF | 821 | 52.63% | + |   | + | + |   |   | + | + |
| | GCCAAGTGTAAGACGCAGT | 47 | 4 | ORF | 484 | 52.63% | + | + |   |   |   |   | + | + |
| | TCTGGCAGTCTTCCAGTGT | 48 | 4 | ORF | 182 | 52.63% | + | + |   |   |   |   | + | + |
| | CATCCATGGCTACGTTGAC | 49 | 4 | ORF | 819 | 52.63% | + | + | + |   |   |   |   | + |
| | CAAGTGTAAGACGCAGTAC | 50 | 4 | ORF | 486 | 47.37% | + | + | + | + |   |   |   |   |
| | ATCCATGGCTACGTTGACG | 51 | 3 | ORF | 820 | 52.63% | + | + |   |   | + |   |   |   |
| sirt7 | CCAAATACTTGGTCGTCTA | 51 | 7 | ORF | 329 | 42.11% | + | + |   | + | + | + | + | + |
| | CGAAGCTTTACATCGTGAA | 52 | 7 | ORF | 905 | 42.11% | + | + | + | + | + |   | + | + |
| | GTCCGGAACGCCAAATACT | 53 | 6 | ORF | 319 | 52.63% | + | + | + |   |   |   | + | + |
| | AAATACTTGGTCGTCTACA | 54 | 6 | ORF | 331 | 36.84% | + | + | + | + | + |   | + |   |
| | CATGTGGTGTCTCAGAACT | 55 | 6 | ORF | 520 | 47.37% | + | + | + |   |   | + | + | + |
| | GGCCGAAGCTTTACATCGT | 56 | 6 | ORF | 902 | 52.63% | + | + | + |   |   | + | + | + |
| | CCGAAGCTTTACATCGTGA | 57 | 6 | ORF | 904 | 47.37% | + |   | + | + |   | + | + | + |
| | TCCGGAACGCCAAATACTT | 58 | 6 | ORF | 320 | 47.37% | + | + | + |   |   |   | + | + |
| | TGTGGTGTCTCAGAACTGT | 59 | 5 | ORF | 522 | 47.37% | + | + | + |   |   |   | + | + |
| | CAAATACTTGGTCGTCTAC | 60 | 5 | ORF | 330 | 42.11% | + | + | + |   | + |   |   | + |
| | GGAAGTGTGATGACGTCAT | 61 | 5 | ORF | 971 | 47.37% | + | + |   |   | + |   | + | + | siRNA molecules were designed according to the Dharmacon design center:
http://www.dharmacon.com/sidesign/
Criteria: The Reynolds rules TABLE 1-continued

| siRNA target sequence | Seq id no: | Score | Region | Start | GC Content | 1 | 2 | 3 | 4 | 5 | 6 | 7 | 8 |
|---|---|---|---|---|---|---|---|---|---|---|---|---|---|

1. 30%-52% GC Content
2. At least 3 A/Us at positions 15-19 (sense)
3. Absence of internal repeats
4. A at position 19 (sense)
5. A at position 3 (sense)
6. U at position 10 (sense)
7. No G/C at position 19 (sense)
8. No G at position 13 (sense)

Another agent capable of downregulating Sir2 expression is a DNAzyme molecule, which is capable of specifically cleaving an mRNA transcript or a DNA sequence of the Sir2 protein. DNAzymes are single-stranded polynucleotides that are capable of cleaving both single- and double-stranded target sequences (Breaker, R. R. and Joyce, G. F. (1995). A DNA enzyme with $Mg^{2+}$-dependent RNA phosphoesterase activity. Curr Biol 2, 655-660; Santoro, S. W. and Joyce, G. F. (1997). A general purpose RNA-cleaving DNA enzyme. Proc Natl Acad Sci USA 94, 4262-4266). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro and Joyce (1997)); for review of DNAzymes, see: Khachigian, L. M. (2002). DNAzymes: cutting a path to a new class of therapeutics. Curr Opin Mol Ther 4, 119-121.

Examples of construction and amplification of synthetic, engineered DNAzymes recognizing single- and double-stranded target cleavage sites are disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh, T. et al., Abstract 409, American Society of Gene Therapy 5th Annual Meeting (www.asgt.org), Jun. 5-9, 2002, Boston, Mass. USA.). In another application, DNAzymes complementary to bcr-abl oncogenes were successful in inhibiting the oncogene's expression in leukemia cells, and in reducing relapse rates in autologous bone marrow transplants in cases of Chronic Myelogenous Leukemia (CML) and Acute Lymphoblastic Leukemia (ALL).

Another agent capable of downregulating Sir2 expression is a ribozyme molecule capable of specifically cleaving an mRNA transcript encoding a Sir2 protein. Ribozymes increasingly are being used for the sequence-specific inhibition of gene expression by the cleavage of mRNAs encoding proteins of interest (Welch, P. J. et al. (1998). Expression of ribozymes in gene transfer systems to modulate target RNA levels. Curr Opin Biotechnol 9, 486-496). The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers, and specific somatic mutations in genetic disorders (Welch, P. J. et al. (1998). Ribozyme gene therapy for hepatitis C virus infection. Clin Diagn Virol 10, 163-171). Most notably, several ribozyme gene therapy protocols for HIV patients are already in Phase 1 trials. More recently, ribozymes have been used for transgenic animal research, gene target validation, and pathway elucidation.

Several ribozymes are in various stages of clinical trials. ANGIOZYME™ was the first chemically synthesized ribozyme to be studied in human clinical trials. ANGIOZYME specifically inhibits formation of the VEGFR (Vascular Endothelial Growth Factor receptor), a key component in the angiogenesis pathway. Ribozyme Pharmaceuticals, Inc., as well as other firms, has demonstrated the importance of anti-angiogenesis therapeutics in animal models. HEPTAZYME™, a ribozyme designed to selectively destroy Hepatitis C Virus (HCV) RNA, was found effective in decreasing Hepatitis C viral RNA in cell culture assays (Ribozyme Pharmaceuticals, Inc., Boulder, Colo., USA (www.rpi.com)).

An additional method of regulating the expression of a Sir2 gene in cells is via triplex-forming oligonucleotides (TFOs). Recent studies show that TFOs can be designed to recognize and bind to polypurine or polypirimidine regions in double-stranded helical DNA in a sequence-specific manner. These recognition rules are outlined in: Maher III, L. J., et al. (1989). Inhibition of DNA binding proteins by oligonucleotide-directed triple helix formation. Science 245, 725-730; Moser, H. E., et al. (1987). Sequence-specific cleavage of double helical DNA by triple helix formation. Science 238, 645-650; Beal, P. A. and Dervan, P. B. (1991). Second structural motif for recognition of DNA by oligonucleotide-directed triple-helix formation. Science 251, 1360-1363; Cooney, M., et al. (1988). Science 241, 456-459; and Hogan, M. E., et al., EP Publication 375408. Modifications of the oligonucleotides, such as the introduction of intercalators and backbone substitutions, and optimization of binding conditions (e.g., pH and cation concentration) have aided in overcoming inherent obstacles to TFO activity such as charge repulsion and instability, and it was recently shown that synthetic oligonucleotides can be targeted to specific sequences (for a recent review, see Seidman, M. M. and Glazer, P. M. (2003). The potential for gene repair via triple helix formation J Clin Invest 112, 487-494).

In general, the triplex-forming oligonucleotide has the sequence correspondence:

```
oligo    3'--A    G    G    T
duplex   5'--A    G    C    T
duplex   3'--T    C    G    A
```

However, it has been shown that the A-AT and G-GC triplets have the greatest triple-helical stability (Reither, S, and Jeltsch, A. (2002). Specificity of DNA triple helix formation analyzed by a FRET assay. BMC Biochem 3(1), 27, Epub). The same authors have demonstrated that TFOs designed according to the A-AT and G-GC rule do not form nonspecific triplexes, indicating that triplex formation is indeed sequence-specific.

Thus, a triplex-forming sequence may be devised for any given sequence in the Sir2 regulatory region. Triplex-forming oligonucleotides preferably are at least 15, more preferably 25, still more preferably 30 or more, nucleotides in length, up to 50 or 100 bp.

Transfection of cells with TFOs (for example, via cationic liposomes) and formation of the triple-helical structure with the target DNA induces steric and functional changes, blocking transcription initiation and elongation, allowing the introduction of desired sequence changes in the endogenous DNA, and resulting in the specific downregulation of gene expression. Examples of suppression of gene expression in cells treated with TFOs include: knockout of episomal supFG1 and endogenous HPRT genes in mammalian cells (Vasquez, K. M. et al. (1999). Chromosomal mutations induced by triplex-forming oligonucleotides in mammalian cells. Nucd Acids Res 27, 1176-1181; and Puri, N. et al. (2001). Targeted Gene Knockout by 2'-O-Aminoethyl Modified Triplex Forming Oligonucleotides. J Biol Chem 276, 28991-28998); the sequence- and target-specific downregulation of expression of the Ets2 transcription factor, important in prostate cancer etiology (Carbone, G. M. et al., Selective inhibition of transcription of the Ets2 gene in prostate cancer cells by a triplex-forming oligonucleotide. Nucl Acids Res 31, 833-843); and regulation of the pro-inflammatory ICAM-1 gene (Besch, R. et al. (2003). Specific inhibition of ICAM-1 expression mediated by gene targeting with Triplex-forming oligonucleotides. J Biol Chem 277, 32473-32479). In addition, Vuyisich and Beal have recently shown that sequence-specific TFOs can bind to dsRNA, inhibiting activity of dsRNA-dependent enzymes such as RNA-dependent kinases (Vuyisich, M. and Beal, P. A. (2000). Regulation of the RNA-dependent protein kinase by triple helix formation. Nucl Acids Res 28, 2369-2374).

Additionally, TFOs designed according to the abovementioned principles can induce directed mutagenesis capable of effecting DNA repair, thus providing both downregulation and upregulation of expression of endogenous genes (Seidman and Glazer (2003)). Detailed description of the design, synthesis, and administration of effective TFOs can be found in U.S. patent application Ser. Nos. 03/017,068 and 03/0,096,980 to Froehler et al. and 02/0,128,218 and 02/0,123,476 to Emanuele et al., and U.S. Pat. No. 5,721,138 to Lawn.

Peptide inhibitors—Competitive peptide inhibitors may be derived from any Sir2 substrate (such as described in the background section), typically derived from the substrate recognition site (i.e., acetylated sequence). Such peptide inhibitors are well known in the art. For example, a peptide sequence modeled after the acetylation site of p53 is described by Marcotte (2004) Anal. Biochem. 332(1):90-9. Alternatively, the H4 peptide (available from Upstate Biotechnology), typically used for measuring deacetylase activity of Sir2, as described by Dryden Mol. Cell. Biol. 23:3173-85. Other peptide inhibitors with improved bioavailability and/or affinity towards Sir2 protein or effector may be generated using methods which are well known in the art, such as computational modeling and phage display.

Non-functional forms of SIRs—Naturally occurring or genetically modified forms of SIRs may be used to downregulate the activity of endogenous Sir2, preferably in a dominant negative manner. For example, H232 SIRT2 mutant protein is devoid of SIRT2 deacetylase activity. Construction and characterization of this SIRT2 mutant is described in length by Dryden Mol. Cell. Biol. 23:3173-85.

Antibody inhibitors—A neutralizing antibody agent which binds, for example the Sir2 catalytic domain or regulatory sequences (typically located N-terminally or C-terminally to the catalytic core), thereby inhibiting Sir2 catalytic activity may be used in accordance with the present invention. For example, such an antibody may be directed at Histidine 150 which is crucial for SIRT2 deacetylation activity. It will be appreciated, though, that since Sir2 is an intracellular protein, measures are taken to use antibody agents which may be delivered through the plasma membrane. In this respect a fragmented antibody such as a Fab fragment (described hereinunder), or a genetically engineered ScFv is preferably used.

The term "antibody" as used in this invention includes intact molecules as well as functional fragments thereof, such as Fab, F(ab')$_2$, and Fv that are capable of binding to macrophages. These functional antibody fragments are defined as follows:

Fab, the fragment which contains a monovalent antigen-binding fragment of an antibody molecule, can be produced by digestion of whole antibody with the enzyme papain to yield an intact light chain and a portion of one heavy chain;

Fab', the fragment of an antibody molecule that can be obtained by treating whole antibody with pepsin, followed by reduction, to yield an intact light chain and a portion of the heavy chain; two Fab' fragments are obtained per antibody molecule;

(Fab')$_2$, the fragment of the antibody that can be obtained by treating whole antibody with the enzyme pepsin without subsequent reduction; F(ab')$_2$ is a dimer of two Fab' fragments held together by two disulfide bonds;

Fv, defined as a genetically engineered fragment containing the variable region of the light chain and the variable region of the heavy chain expressed as two chains; and Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

Antibody fragments according to the present invention can be prepared by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. Anti-Sir2 antibodies are known in the art. See for Example, the antibodies described by Gotta (1997) EMBO J. 16:3243-55; Straight (1999) Cell 97:245-56; and Dryden (2003) Mol. Cell. Biol. 23:3173-85.

Fv fragments comprise an association of $V_H$ and $V_L$ chains.

This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv or scFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins recipient antibody in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Protein agents (e.g., antibodies, peptides, non-functional Sir2 proteins) and oligonucleotide agents (ribozymes, DNAzymes, RNAi, etc.) of the present invention can be expressed from a polynucleotide encoding same and provided to ex-vivo cultured stem cells employing an appropriate gene delivery vehicle/method and a nucleic acid construct as is further described hereinunder.

Expression of such constructs can be transient or stable expression. Thus, according to one embodiment of the present invention, providing the agent of the present invention is effected by transiently expressing the antisense polynucleotide, the ribozyme, the siRNA molecule or the DNAzyme within a stem cell. In another, preferred embodiment, the expression is stable, and providing is effected by (a) providing an expressible polynucleotide capable of expressing the antisense polynucleotide, the ribozyme, the siRNA molecule or the DNAzyme and, (b) stably integrating the expressible polynucleotide into a genome of a cell, thereby providing agent capable of downregulating a Sir2 activity or expression. Suitable constructs and methods for their stable and transient expression in cells are described hereinbelow.

Examples of suitable constructs include, but are not limited to pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Various methods can be used to introduce the expression constructs of the present invention into stem cells. Such methods are generally described in, for instance: Sambrook, J. and Russell, D. W. (1989, 1992, 2001), Molecular Cloning: A Laboratory Manual, Cold Springs Harbor Laboratory, New York; Ausubel, R. M. et al., eds. (1994, 1989). Current Protocols in Molecular Biology, John Wiley and Sons, Baltimore, Md. (1989); Chang, P. L., ed. (1995). Somatic Gene Therapy, CRC Press, Boca Raton, Fla.; Vega, M. A. (1995). Gene Targeting, CRC Press, Boca Raton, Fla.; Rodriguez, R. L. and Denhardt, D. H. (1987). Vectors: A Survey of Molecular Cloning Vectors and Their Uses, Butterworth-Heinemann, Boston, Mass.; and Gilboa, E. et al. (1986). Transfer and expression of cloned genes using retro-viral vectors. Biotechniques 4(6), 504-512; and include, for example, stable or transient transfection, lipofection, electroporation, and infection with recombinant viral vectors. In addition, see U.S. Pat. Nos. 5,464,764 and 5,487,992 for positive-negative selection methods.

Final concentrations of the agents of the present invention may be, depending on the specific application, as well as on the nature of the agent, in the nanomolar to millimolar ranges. For example, within about 1 nM to about 500 mM, preferably within about 10 nM to about 200 mM, more preferably within about 1 nM to about 1 mM. The cultures are treated with the agent for up to three-weeks only or for as long as the cells are in culture.

While reducing the present invention to practice, effective inhibition of $CD34^+$ hematopoietic stem cells differentiation, and renewal of the $CD34^+$ population was demonstrated in cells provided with the Sir2 inhibitor, splitomicin, in an effective concentration of 200 mM.

To improve differentiation-less expansion of stem cells according to the teachings of the present invention, culturing of stem cells with the present agents may be effected in the presence of other differentiation inhibiting agents which are well known in the art. Examples of differentiation inhibiting agents which may be used in accordance with the present invention, include, but are not limited to, nicotineamide, PI3-Kinase inhibitors, RAR-antagonists (such as disclosed in WO/03062369).

The teachings of this aspect of the present invention, can be utilized for expanding a population of hematopoietic renewable stem cells ex-vivo.

Hence, according to another aspect of the present invention, there is provided a method of ex-vivo expanding a population of hematopoietic renewable stem cells ex-vivo. The method is effected by obtaining adult or neonatal umbilical cord whole white blood cells (also known in the art as mononuclear cell fraction) or whole bone marrow cells sample and providing the cells in the sample with ex-vivo culture conditions for stem cells ex-vivo cell proliferation and, at the same time, for reducing the expression and/or activity of Sir2, as is described hereinabove, thereby expanding a population of a renewable stem cells in the sample.

In still another particular embodiment of this aspect of the present invention, the method is effected by obtaining adult or neonatal umbilical cord whole white blood cells or whole bone marrow cells sample and providing the cells in the sample with ex-vivo culture conditions for stem cells ex-vivo cell proliferation and, at the same time, for reducing a capacity of the stem cells in responding to Sir2 activity, thereby expanding a population of a renewable stem cells in the sample.

In still another particular embodiment of this aspect of the present invention, the method is effected by obtaining adult or neonatal umbilical cord whole white blood cells or whole bone marrow cells sample and providing the cells in the sample with ex-vivo culture conditions for stem cells ex-vivo cell proliferation and with a Sir2 inhibitor, thereby expanding a population of a renewable stem cells in the sample.

Expanding the population of stem cells can be further utilized, according to the present invention, in in vivo settings, such that according to yet another aspect of the present invention there is provided a method of in-vivo expanding a population of stem cells, while at the same time, substantially inhibiting differentiation of the stem cells in-vivo. The method, according to this aspect of the present invention is effected by administering to a subject in need thereof a therapeutically effective amount of at least one of the agents described hereinabove.

As used herein throughout, the phrase "therapeutically effective amount" or "effective amount" refers to that amount of the agent being administered which will induce expansion of stem cells yet inhibit the differentiation thereof.

The methods described hereinabove for ex-vivo expanding stem cells populations can result, inter alia, in an expanded population of stem cells.

Thus, further according to an aspect of the present invention there is provided an ex-vivo expanded population of hematopoietic stem cells which comprises a plurality of cells characterized by 3-20% of the cells being reselectable $CD34^+$ cells, of which at least 40% of cells are $CD34^+_{dim}$, i.e., fall below the median intensity in a FACS analysis, wherein, in the reselectable $CD34^+$ cells, a majority of cells which are $Lin^-$ are also $CD34^+$ dim cells. In one embodiment, the hematopoietic stem cells are derived from a source selected from the group consisting of bone marrow, peripheral blood and neonatal umbilical cord blood. In another embodiment, the population of cells has a single genetic background. In yet another embodiment, the ex-vivo expanded population of hematopoietic stem cells comprises at least N cells derived from a single donor, wherein N equals the average number of $CD34^+$ cells derived from one sample of neonatal umbilical cord blood, bone marrow, or peripheral blood multiplied by 1,000. Cell surface expression of the CD34 and/or Lin markers can be determined, for example, via FACS analysis or immunohistological staining techniques. A self renewal potential of the stem cells can be determined in-vitro by long term colony formation (LTC-CFUc), as is further exemplified in the Examples section that follows, or by in-vivo engraftment in the SCID-Hu mouse model. The SCID-Hu mouse model employs C.B-17 scid/scid (SCID) mice transplanted with human fetal thymus and liver tissue or fetal BM tissue and provides an appropriate model for the evaluation of putative human hematopoietic stem cells. Because of the reconstitution of the SCID mice with human fetal tissue, the model affords the proliferation of stem cells, in this case human hematopoietic stem cells to proliferate, and function in the hematopoietic microenvironment of human origin. Mice are typically irradiated, then delivered stem cells into the grafts, and reconstitution is measured by any number of methods, including FACS and immunohistochemistry of repopulated organs (Humeau L., et al. Blood (1997) 90:3496).

Additionally, the methods described hereinabove can be utilized to produce transplantable hematopoietic cell preparations, such that according to yet another aspect of the present invention there is provided a therapeutic ex vivo cultured stem cell population, which comprises an undifferentiated hematopoietic cells expanded ex-vivo in the presence of an effective amount of an agent, as described hereinabove. It will be appreciated, in the context of the present invention, that the therapeutic stem cell population can be provided along with the culture medium containing the agent, isolated from the culture medium, and combined with a pharmaceutically acceptable carrier. Hence, cell populations of the invention can be administered in a pharmaceutically acceptable carrier or diluent, such as sterile saline and aqueous buffer solutions. The use of such carriers and diluents is well known in the art.

In one particular embodiment of this aspect of the present invention, the therapeutic ex vivo cultured stem cell population comprises an expanded population of hematopoietic stem cells propagated ex-vivo in the presence of an effective amount of an agent, which reduces a capacity of the stem cells in responding to Sir2 activity, substantially inhibiting differentiation of the stem cells; and a pharmaceutically acceptable carrier.

In still another particular embodiment of this aspect of the present invention, the transplantable hematopoietic cell preparation comprises an expanded population of hematopoietic stem cells propagated ex-vivo in the presence of an effective amount of the above-described agent, and a pharmaceutically acceptable carrier.

The ability of the agents of the present invention to inhibit differentiation of stem cells can be further used in various technical applications:

According to a further aspect of the present invention there is provided a method of preserving stem cells. In one embodiment, the method is effected by handling the stem cell in at least one of the following steps: harvest, isolation and/or storage, in a presence of an effective amount of at least one of the above described agents.

According to still a further aspect of the present invention there is provided a cells collection/culturing bag. The cells collection/culturing bag of the present invention is supplemented with an effective amount of at least one of the above described agents.

According to the present invention there is also provided a cells separation and/or washing buffer. The separation and/or washing buffer is supplemented with an effective amount of at least one of the above-described agents.

As is further detailed below, stem cells may serve to exert cellular gene therapy.

Gene therapy as used herein refers to the transfer of genetic material (e.g., DNA or RNA) of interest into a host to treat or prevent a genetic or acquired disease or condition or phenotype. The genetic material of interest encodes a product (e.g., a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (i) ex-vivo or cellular gene therapy; and (ii) in vivo gene therapy. In ex-vivo gene therapy cells are removed from a patient, and while being cultured are treated in-vitro. Generally, a functional replacement gene is introduced into the cells via an appropriate gene delivery vehicle/method (transfection, transduction, homologous recombination, etc.) and an expression system as needed and then the modified cells are expanded in culture and returned to the host/patient. These genetically re-implanted cells have been shown to express the transfected genetic material in situ.

Hence, further according to an aspect of the present invention, there is provided a method of transducing expanded, undifferentiated stem cells with an exogene. The method, according to this aspect of the present invention, is effected by: (a) obtaining a population of stem cells to be transduced; (b) expanding and inhibiting differentiation of the stem cells by: (i) providing the stem cells with conditions for cell proliferation and (ii) providing the stem cells with an effective concentration of a modulator of PI 3-kinase activity, said modulator selected capable of downregulating a PI 3-kinase activity or an expression of a gene encoding a PI 3-kinase, thereby expanding and inhibiting differentiation of the stem cells; and (c) transducing the expanded, undifferentiated stem cells with the exogene. It will be appreciated that steps (i) and (ii) can be effected in vitro or ex vivo, and that the order of steps (b) and (c) can be reversed.

In another particular embodiment of this aspect of the present invention, step (ii) is effected by reducing a capacity of the stem cells in responding to signaling pathways involving PI 3-kinase, thereby expanding and inhibiting differentiation of the stem cells.

In a preferred embodiment, genetically modifying the cells is effected by a vector, which comprises the exogene or transgene, which vector is, for example, a viral vector or a nucleic acid vector. Many viral vectors suitable for use in cellular gene therapy are known, examples are provided hereinbelow. Similarly, a range of nucleic acid vectors can be used to genetically transform the expanded cells of the invention, as is further described below.

Accordingly, the expanded cells of the present invention can be modified to express a gene product. As used herein, the phrase "gene product" refers to proteins, peptides and functional RNA molecules. Generally, the gene product encoded by the nucleic acid molecule is the desired gene product to be supplied to a subject. Examples of such gene products include proteins, peptides, glycoproteins and lipoproteins normally produced by an organ of the recipient subject. For example, gene products which may be supplied by way of gene replacement to defective organs in the pancreas include insulin, amylase, protease, lipase, trypsinogen, chymotrypsinogen, carboxypeptidase, ribonuclease, deoxyribonuclease, triacylglycerol lipase, phospholipase A2, elastase, and amylase; gene products normally produced by the liver include blood clotting factors such as blood clotting Factor VIII and Factor IX, UDP glucuronyl transferae, ornithine transcarbanoylase, and cytochrome p450 enzymes, and adenosine deaminase, for the processing of serum adenosine or the endocytosis of low density lipoproteins; gene products produced by the thymus include serum thymic factor, thymic humoral factor, thymopoietin, and thymosin α1; gene products produced by the digestive tract cells include gastrin, secretin, cholecystokinin, somatostatin, serotinin, and substance P.

Alternatively, the encoded gene product is one, which induces the expression of the desired gene product by the cell (e.g., the introduced genetic material encodes a transcription factor, which induces the transcription of the gene product to be supplied to the subject).

In still another embodiment, the recombinant gene can provide a heterologous protein, e.g., not native to the cell in which it is expressed. For instance, various human MHC components can be provided to non-human cells to support engraftment in a human recipient. Alternatively, the transgene is one, which inhibits the expression or action of a donor MHC gene product normally expressed in the micro-organ explant.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the gene acid molecule include promoters, enhancers and polyadenylation signals, as well as sequences necessary for transport of an encoded protein or peptide, for example N-terminal signal sequences for transport of proteins or peptides to the surface of the cell or secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements, which are known in the art, include upstream regions from the dystrophin gene (Klamut et al., (1989) *Mol. Cell. Biol.* 9: 2396), the creatine kinase gene (Buskin and Hauschka, (1989) *Mol. Cell Biol.* 9: 2627) and the troponin gene (Mar and Ordahl, (1988) *Proc. Natl. Acad. Sci. USA*. 85: 6404). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters).

Alternatively, a regulatory element, which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs.

Alternatively, a regulatory element, which provides inducible expression of a gene linked thereto, can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S, and White, J. H. (1993) *Proc. Natl. Acad. Sci. USA* 90: 5603-5607), synthetic ligand-regulated elements (see, e.g., Spencer, D. M. et al. 1993)*Science* 262: 1019-1024) and ionizing radiation-regulated elements (e.g., see Manome, Y. Et al. (1993) *Biochemistry* 32: 10607-10613; Datta, R. et al. (1992) *Proc. Natl. Acad. Sci. USA* 89: 1014-10153). Additional tissue-specific or inducible regulatory systems, which may be developed, can also be used in accordance with the invention.

There are a number of techniques known in the art for introducing genetic material into a cell that can be applied to modify a cell of the invention.

In one embodiment, the nucleic acid is in the form of a naked nucleic acid molecule. In this situation, the nucleic acid molecule introduced into a cell to be modified consists only of the nucleic acid encoding the gene product and the necessary regulatory elements.

Alternatively, the nucleic acid encoding the gene product (including the necessary regulatory elements) is contained within a plasmid vector. Examples of plasmid expression vectors include CDM8 (Seed, B. (1987) *Nature* 329: 840) and pMT2PC (Kaufman, et al. (1987)*EMBO J* 6: 187-195).

In another embodiment, the nucleic acid molecule to be introduced into a cell is contained within a viral vector. In this situation, the nucleic acid encoding the gene product is inserted into the viral genome (or partial viral genome). The regulatory elements directing the expression of the gene product can be included with the nucleic acid inserted into the viral genome (i.e., linked to the gene inserted into the viral genome) or can be provided by the viral genome itself.

Naked nucleic acids can be introduced into cells using calcium-phosphate mediated transfection, DEAE-dextran mediated transfection, electroporation, liposome-mediated transfection, direct injection, and receptor-mediated uptake.

Naked nucleic acid, e.g., DNA, can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. $CaPO_4$-mediated transfection can be used to stably (or transiently) transfect cells and is only applicable to in vitro modification of cells. Protocols for $CaPO_4$-mediated transfection can be found in Current Protocols in Molecular Biology, Ausubel, F. M. et al. (eds.) Greene Publishing Associates, (1989), Section 9.1 and in Molecular Cloning: A Laboratory Manual, 2nd Edition, Sambrook et al. Cold Spring Harbor Laboratory Press, (1989), Sections 16.32-16.40 or other standard laboratory manuals.

Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce DNA transiently into cells but is not preferred for creating stably transfected cells. Thus, this method can be used for short-term production of a gene product but is not a method of choice for long-term production of a gene product. Protocols for DEAE-dextran-mediated transfection can be found in Current Protocols in Molecular Biology, Ausubel, F. M. et al. (eds.) Greene Publishing Associates (1989), Section 9.2 and in Molecular Cloning: A Laboratory Manual, 2nd Edition, Sambrook et al. Cold Spring Harbor Laboratory Press, (1989), Sections 16.41-16.46 or other standard laboratory manuals.

Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the DNA and the ionic composition of the media. Electroporation can be used to stably (or transiently) transfect a wide variety of cell types and is only applicable to in vitro modification of cells. Protocols for electroporating cells can be found in Current Protocols in Molecular Biology, Ausubel F. M. et al. (eds.) Greene Publishing Associates, (1989), Section 9.3 and in Molecular Cloning: A Laboratory Manual, 2nd Edition, Sambrook et al. Cold Spring Harbor Laboratory Press, (1989), Sections 16.54-16.55 or other standard laboratory manuals.

Another method by which naked nucleic acid can be introduced into cells includes liposome-mediated transfection (lipofection). The nucleic acid is mixed with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel F. M. et al. (eds.) Greene Publishing Associates, (1989), Section 9.4 and other standard laboratory manuals. Additionally, gene delivery in vivo has been accomplished using liposomes. See for example Nicolau et al. (1987)*Meth. Enz.* 149:157-176; Wang and Huang (1987) *Proc. Natl. Acad. Sci.* USA 84:7851-7855; Brigham et al. (1989)*Am. J. Med. Sci.* 298:278; and Gould-Fogerite et al. (1989)*Gene* 84:429-438.

Naked nucleic acid can also be introduced into cells by directly injecting the nucleic acid into the cells. For an in vitro culture of cells, DNA can be introduced by microinjection. Since each cell is microinjected individually, this approach is very labor intensive when modifying large numbers of cells.

However, a situation wherein microinjection is a method of choice is in the production of transgenic animals (discussed in greater detail below). In this situation, the DNA is stably introduced into a fertilized oocyte, which is then allowed to develop into an animal. The resultant animal contains cells carrying the DNA introduced into the oocyte. Direct injection has also been used to introduce naked DNA into cells in vivo (see e.g., Acsadi et al. (1991) *Nature* 332:815-818; Wolff et al. (1990)*Science* 247:1465-1468). A delivery apparatus (e.g., a "gene gun") for injecting DNA into cells in vivo can be used. Such an apparatus is commercially available (e.g., from Bio-Rad).

Naked nucleic acid can be complexed to a cation, such as polylysine, which is coupled to a ligand for a cell-surface receptor to be taken up by receptor-mediated endocytosis (see for example Wu, G. and Wu, C. H. (1988) *J. Biol. Chem.* 263: 14621; Wilson et al. (1992)*J. Biol. Chem.* 267: 963-967; and U.S. Pat. No. 5,166,320). Binding of the nucleic acid-ligand complex to the receptor facilitates uptake of the DNA by receptor-mediated endocytosis. Receptors to which a DNA-ligand complex has targeted include the transferrin receptor and the asialoglycoprotein receptor. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88: 8850; Cristiano et al. (1993) *Proc. Natl. Acad. Sci. USA* 90: 2122-2126). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Generally, when naked DNA is introduced into cells in culture (e.g., by one of the transfection techniques described above) only a small fraction of cells (about 1 out of $10^5$) typically integrate the transfected DNA into their genomes (i.e., the DNA is maintained in the cell episomally). Thus, in order to identify cells, which have taken up exogenous DNA, it is advantageous to transfect nucleic acid encoding a selectable marker into the cell along with the nucleic acid(s) of interest. Preferred selectable markers include those, which confer resistance to drugs such as G418, hygromycin and methotrexate. Selectable markers may be introduced on the same plasmid as the gene(s) of interest or may be introduced on a separate plasmid.

A preferred approach for introducing nucleic acid encoding a gene product into a cell is by use of a viral vector containing nucleic acid, e.g., a cDNA, encoding the gene product. Infection of cells with a viral vector has the advantage that a large proportion of cells receive the nucleic acid which can obviate the need for selection of cells which have received the nucleic acid. Additionally, molecules encoded within the viral vector, e.g., a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for review see Miller, A. D. (1990) *Blood* 76: 271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions, which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM, which are well known to those skilled in the art. Examples of suitable packaging virus lines include ψCrip, ψCrip, ψ2 and ψAm. Retroviruses have been used to introduce a variety of genes into many different cell types, including epithelial cells endothelial cells, lymphocytes, myoblasts, hepatocytes, bone marrow cells, in vitro and/or in vivo (see for example Eglitis, et al. (1985) Science 230: 1395-1398; Danosand Mulligan (1988) *Proc. Natl. Acad. Sci. USA* 85: 6460-6464; Wilson et al. (1988) *Proc. Natl. Acad. Sci. USA* 85:3014-3018; Armentano et al., (1990) Proc. Natl. Acad. Sci. USA 87: 6141-6145; Huber et al. (1991) Proc. Natl. Acad. Sci. USA 88: 8039-8043; Feri et al. (1991) Proc. Natl. Acad. Sci. USA 88:8377-8381; Chowdhury et al. (1991) *Science* 254: 1802-1805; van Beusechem et al. (1992) Proc. Natl. Acad. Sci USA 89:7640-7644; Kay et al. (1992)*Human Gene Therapy* 3:641-647; Dai et al. (1992) *Proc. Natl. Acad. Sci. USA* 89:10892-10895; Hwu et al. (1993) J. Immunol. 150:4104-4115; U.S. Pat. No. 4,868,116; U.S. Pat. No. 4,980, 286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

The genome of an adenovirus can be manipulated such that it encodes and expresses a gene product of interest but is inactivated in terms of its ability to replicate in a normal lytic viral life cycle. See for example Berkner et al. (1988) *Bio-Techniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89: 6482-6486), hepatocytes (Herz and Gerard (1993) *Proc. Natl. Acad. Sci. USA* 90: 2812-2816) and muscle cells (Quantin et al. (1992) *Proc. Natl. Acad. Sci. USA* 89: 2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986)*J Virol* 57: 267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics In Micro. And Immunol.* (1992) 158: 97-129). It is also one of the few viruses that may integrate its DNA into non-dividing cells, and exhibits a high frequency of stable integration (see for example Flotte et al. (1992) *Am. J. Respir. Cell. Mol. Biol.* 7: 349-356; Samulski et al. (1989) *J. Virol.* 63:3822-3828; and McLaughlin et al. (1989) J. Virol. 62: 1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5: 3251-3260 can be used to introduce DNA into cells. A variety of nucleic acids have been introduced into different cell types using AAV vectors (see for example Hermonat et al. (1984) *Proc. Natl. Acad. Sci. USA* 81: 6466-6470; Tratschin et al. (1985) *Mol. Cell. Biol.* 4: 2072-2081; Wondisford et al. (1988) *Mol. Endocrinol.* 2:32-39; Tratschin et al. (1984) *J. Virol.* 51: 611-619; and Flotte et al. (1993) J. Biol. Chem. 268: 3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone.

When the method used to introduce nucleic acid into a population of cells results in modification of a large proportion of the cells and efficient expression of the gene product by the cells (e.g., as is often the case when using a viral expression vector), the modified population of cells may be used without further isolation or subcloning of individual cells within the population. That is, there may be sufficient production of the gene product by the population of cells such that no further cell isolation is needed. Alternatively, it may be desirable to grow a homogenous population of identically modified cells from a single modified cell to isolate cells, which efficiently express the gene product. Such a population of uniform cells can be prepared by isolating a single modified cell by limiting dilution cloning followed by expanding the single cell in culture into a clonal population of cells by standard techniques.

As is discussed in detail hereinabove, ex-vivo expansion of stem cells can be advantageously utilized in hematopoietic cells transplantation or implantation. Hence, according to another aspect of the present invention there is provided a method of hematopoietic cells transplantation or implantation into a recipient. The method according to this aspect of the present invention is effected by (a) obtaining a population of hematopoietic stem cells to be transplanted; (b) ex-vivo expanding and inhibiting differentiation of the hematopoietic stem cells by: (i) ex vivo providing said stem cells with conditions for cell proliferation, and (ii) providing said stem cells with an effective concentration of an agent capable of down-regulating activity and/or expression of a Sir2 protein and/or a down-stream effector thereof (agent of the present invention); thereby expanding and inhibiting differentiation of said stem cells; and (c) transplanting or implanting the hematopoietic stem cells into a recipient.

The donor and the recipient can be a single individual or different individuals, for example, allogeneic individuals. When allogeneic transplantation is practiced, regimes for reducing implant rejection and/or graft vs. host disease, as well known in the art, should be undertaken. Such regimes are currently practiced in human therapy. Most advanced regimes are disclosed in publications by Slavin S. et al., e.g., J Clin Immunol (2002) 22: 64, and J Hematother Stem Cell Res (2002) 11: 265), Gur H. et al. (Blood (2002) 99: 4174), and Martelli M F et al, (Semin Hematol (2002) 39: 48), which are incorporated herein by reference.

According to yet another aspect of the present invention there is provided a method of adoptive immunotherapy. The method according to this aspect of the present invention is effected by (a) obtaining progenitor hematopoietic stem cells from a patient; (b) ex-vivo expanding and inhibiting differentiation of the hematopoietic stem cells by: (i) providing the stem cells ex vivo with conditions for cell proliferation, and (ii) providing the progenitor hematopoietic cells with an effective concentration of an agent of the present invention; thereby expanding and inhibiting differentiation of said stem cells; and (c) transplanting or implanting the progenitor hematopoietic stem cells into a recipient.

In another particular embodiment of this aspect of the present invention, step (b) of the method is effected by providing the cells with conditions for reducing a capacity of the stem cells in responding to signaling pathways involving Sir2 activity, thereby expanding a population of the stem cells, while at the same time, substantially inhibiting differentiation of the stem cells.

The effect of the agents that reduce Sir2 expression or activity used in context of the present invention is not limited to ex-vivo settings. Hence, based on the findings herein described, novel in-vivo applications for these agents are envisaged.

Hence, according to yet another aspect of the present invention there is provided a method of mobilization of bone marrow stem cells into the peripheral blood of a donor for harvesting the cells. The method according to this aspect of the present invention is effected by (a) administering to the donor an effective amount of the agent of the present invention and harvesting the cells by leukophoresis.

In still another particular embodiment of this aspect of the present invention, step (a) of the method is effected by administering to the donor an effective amount of an agent for reducing a capacity of the stem cells in responding to Sir2 activity, thereby expanding a and inhibiting differentiation of a population of bone marrow cells.

Preferably, the methods of mobilization of stem cells further comprise administering to the donor at least one cytokine, preferably at least one early cytokine, which are presently used to induce cell mobilization into peripheral blood.

Further according to an aspect of the present invention there is provided a method of inhibiting maturation/differentiation of erythroid precursor cells for the treatment of a β-hemoglobinopathic patient. The method according to this aspect of the present invention is effected by administering to the patient at least one of the agents of the present invention, thereby expanding and inhibiting differentiation of a population of stem cells of the patient, such that upon natural removal of the agent from the patient, the stem cells undergo accelerated maturation, resulting in elevated fetal hemoglobin production.

In in-vivo settings, administration of the agent of the present invention, may be by a pharmaceutical composition including same, which may further include thickeners, carriers, buffers, diluents, surface active agents, preservatives, and the like, all as well known in the art.

The pharmaceutical composition may be administered in various ways, depending on the preference for local or systemic treatment, and on the area to be treated. Administration may be done topically (including opthalmically, vaginally, rectally, intranasally), orally, by inhalation, or parenterally, for example by intravenous drip or intraperitoneal, subcutaneous, subdural, intramuscular or intravenous injection, or via an implantable delivery device.

Formulations for topical administration may include, but are not limited to, lotions, ointments, gels, creams, suppositories, drops, liquids, sprays and powders. Conventional pharmaceutical carriers, aqueous, powder or oily basest thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions, which may also contain buffers, diluents and other suitable additives.

Formulations for implantable delivery devices may similarly include, but are not limited to, sterile solutions, which may also contain buffers, diluents and other suitable additives.

Dosing is dependent on responsiveness of the condition for treatment, but will normally be one or more doses per day, with course of treatment lasting from several days to several months or until a required effect is achieved. Persons ordinarily skilled in the art can easily determine optimum dosages, dosing methodologies and repetition rates. Slow release administration regimes may be advantageous in some applications.

In a recent study (see PCTIL03/00235, to Peled, from which the present application claims priority) the present inventor unexpectedly discovered that ex vivo expanded stem cells differentiate into various cell type, including heart, lung, bone marrow and vascular cells following in vivo administration.

Depending on the source stem cells and target organ, differentiation can be either cis-differentiation or trans-differentiation or a combination of both.

As is mentioned hereinabove "cis-differentiation" refers to differentiation of stem cells into a tissue identical to the tissue from which they were derived. For example, the differentiation of CD34+ hematopoietic cells to different committed/mature blood cells constitutes cis-differentiation.

As is mentioned hereinabove "trans-differentiation" refers to differentiation of stem cells into a tissue distinct from which they were derived. For example, the differentiation of CD34+ hematopoietic cells to cells of different tissue origin, e.g., cardiac cells, constitutes trans-differentiation.

Since the expanded stem cells of the present invention are capable of differentiating in vivo into a variety of specific cell types, and since differentiation can be predetermined according to source and target tissue combinations, the method of the present invention can be utilized in cell replacement therapy.

Since transplantation of cord blood stem cells into MI rats have been shown to result in cell differentiation and homing of differentiated cells to loci of an MI scar and injured lung parenchyma, stem cells, expanded and administered using the methods described hereinabove, can be used to regenerate damaged tissue and in cell replacement therapy. Thus, the present methodology can be used in treating disorders which require cell or tissue replacement.

The disorder can be a neurological disorder, a muscular disorder, a cardiovascular disorder, an hematological disorder, a skin disorder, a liver disorder, and the like.

Myelin disorders form an important group of human neurological diseases that are, as yet, incurable. Progress in animal models, particularly in transplanting cells of the oligodendrocyte lineage, has resulted in significant focal re-myelination and physiological evidence of restoration of function (Repair of myelin disease: Strategies and progress in animal models. Molecular Medicine Today. 1997. pp. 554-561). Future therapies could involve both transplantation and promotion of endogenous repair, and the two approaches could be combined with ex vivo manipulation of donor tissue. Defects in cartilage and bones can also be treated using the teachings of the present invention. Methods of utilizing stem cells for treating such disorders are provided in U.S. Pat. No. 4,642,120. Skin regeneration of a wound or burn in an animal or human can also be treated using the teachings of the present invention. Methods of utilizing stem cells for treating such disorders are provided in U.S. Pat. No. 5,654,186 and U.S. Pat. No. 5,716,411.

In addition to the above-described application, the teachings of the present invention can also be utilized in several other therapeutic applications.

Transplantation of hematopoietic cells has become the treatment of choice for a variety of inherited or malignant diseases. While early transplantation procedures utilized the entire bone marrow (BM) population, recently, more defined populations, enriched for stem cells (CD34+ cells) have been used (Van Epps D E, et al. Harvesting, characterization, and culture of CD34+ cells from human bone marrow, peripheral blood, and cord blood. Blood Cells 20:411, 1994). In addition to bone marrow, such cells could also be derived from other sources such as peripheral blood (PB) and neonatal umbilical cord blood (CB) (Emerson S G. Ex-vivo expansion of hematopoietic precursors, progenitors, and stem cells: The next generation of cellular therapeutics. Blood 87:3082, 1996). Compared to BM, transplantation with PB cells shortens the period of pancytopenia and reduces the risks of infection and bleeding (Brugger W, et al. Reconstitution of hematopoiesis after high-dose chemotherapy by autologous progenitor cells generated in-vivo. N Engl J Med 333: 283, 1995; Williams S F, et al. Selection and expansion of peripheral blood CD34+ cells in autologous stem cell transplantation for breast cancer. Blood 87: 1687, 1996; Zimmerman R M, et al. Large-scale selection of CD34+ peripheral blood progenitors and expansion of neutrophil precursors for clinical applications. J Hematotherapy, 5: 247, 1996).

An additional advantage of using PB for transplantation is its accessibility, although to date the limiting factor in PB transplantation stems from the low number of circulating pluripotent stem/progenitor cells available for harvesting. To obtain enough PB-derived stem cells for transplantation, these cells are "harvested" by repeated leukophoresis following their mobilization from the marrow into the circulation by treatment with chemotherapy and cytokines. Such treatment is obviously not suitable for normal donors. Thus, the use of ex vivo expanded stem cells for transplantation provides several advantages: (i) it reduces the volume of blood required for reconstitution of an adult hematopoietic system and may obviate the need for mobilization and leukophoresis; (ii) it enables storage of small number of PB or CB stem cells for potential future use; and (iii) it traverses contamination limitations often associated with autologous transplantation of recipients with malignancies. In such cases, contaminating tumor cells in autologous infusion often contribute to the recurrence of the disease, selecting and expanding CD34+ stem cells will reduce the load of tumor cells in the final transplant.

In addition, expanded stem cell cultures are depleted of T lymphocytes, and thus are advantageous in allogeneic transplants in which T-cells contribute to graft-versus-host disease (Koller M R, Emerson S G, Palsson B O. Large-scale expansion of human stem and progenitor cells from bone marrow mononuclear cells in continuous perfusion cultures. Blood 82:378, 1993; Lebkowski J S, et al. Rapid isolation and serum-free expansion of human CD34+ cells. Blood Cells 20: 404, 1994).

Clinical studies indicate that transplantation of ex vivo expanded cells derived from a small number of PB CD34+ cells can restore hematopoiesis in recipients treated with high doses of chemotherapy, although the results do not yet allow firm conclusions about long term in vivo hematopoietic capabilities of these cultured cells.

For successful transplantation, shortening the duration of the cytopenic phase, as well as long-term engraftment, is crucial. Inclusion of intermediate and late progenitor cells in the transplant could accelerate the production of donor-derived mature cells thereby shortening the cytopenic phase.

It is thus important, in such applications that ex-vivo expanded cells include, in addition to stem cells, more differentiated progenitor cells in order to optimize short-term recovery and long-term restoration of hematopoiesis. Expansion of intermediate and late progenitor cells, especially those committed to the neutrophilic and megakaryocytic lineages, concomitant with expansion of stem cells, should serve this purpose (Sandstrom C E, et al. Effects of CD34+ cell selection and perfusion on ex vivo expansion of peripheral blood mononuclear cells. Blood 86: 958, 1995). Such cultures may be useful in restoring hematopoiesis in recipients with completely ablated bone marrow, as well as in providing a supportive measure for shortening recipient bone marrow recovery following conventional radio- or chemo-therapies. In addition to the above, the teachings of the present invention can also be applied towards hepatic regeneration, muscle regeneration, and stimulation of bone growth for applications in osteoporosis. The teachings of the present invention can also be applied to cases which require enhanced immune response or replacement of deficient functions, such as, for example, adoptive immunotherapy, including immunotherapy of various malignancies, immuno-deficiencies, viral and genetic diseases [Freedman A R, et al. Generation of T lymphocytes from bone marrow CD34+ cells in vitro. (1996). Nature Medicine. 2: 46; Heslop H E, et al. Long term restoration of immunity against Epstein-Barr virus infection by adoptive transfer of gene-modified virus-specific T lymphocytes. (1996) Nature Medicine, 2: 551; Protti M P, et al. Particulate naturally processed peptides prime a cytotoxic response against human melanoma in vitro. (1996). Cancer Res., 56: 1210].

According to an additional aspect of the present invention, there is provided an assay of determining whether a specific modulator of Sir2 activity or gene expression is capable of inhibiting differentiation of cells. The assay according to this aspect of the present invention comprises culturing a population of cells capable of differentiating, such as stem cells, (e.g. CD34$^+$ hematopoietic cells), progenitor cells, or cells of a substantially non-differentiated cell line, such as, but not limited to, USP-1 and USP-3 (Sukoyan M A (2002) Braz J Med Biol Res, 35(5):535, C6, c2, Cr/A-3, DB1 and B6-26 (U.S. Pat. No. 6,190,910), and H9.1 and H9.2 (Odorico J. S. (2001) Stem Cells 19: 193) in the presence or absence of a test molecule and monitoring changes in differentiation of the cells over time, e.g., a few weeks to a few months. Increased differentiation, as compared to non-treated cells, indicates that the test molecule is incapable of inhibiting differentiation, whereas a lack or decrease in differentiation as compared to untreated cells indicates a the molecule is capable of inhibiting differentiation, which can be used effectively as an inhibitor of Sir2 activity, for example, in the methods of the present invention disclosed herein.

Preferably, culturing the population of stem cells or cells of a substantially non-differentiated cell line is performed in a presence of an effective amount of a cytokine, preferably, an early acting cytokine or a combination of such cytokines, e.g., thrombopoietin (TPO), interleukin-6 (IL-6), an FLT-3 ligand and stem cell factor (SCF).

The results of this assay may be qualified using qualitative and/or quantitative assays for Sir2 activity. Examples of such assays include, but are not limited to, acetate production, such as by using ethyl acetate extraction [see e.g., Kolle et al. (1998) Methods 15:323; Imiliani (1998) Proc. Natl. Acad. Sci. USA 95:2795; Darkin (1996) Proc. Natl. Acad. Sci. USA 93:13143; Hendzel (1991) J. Biol. Chem. 266:21936]; detection of acetylated and de-acetylated substrates, such as by gel electrophoresis, western blot analysis and filter-binding assays. The western blot analysis typically use antibodies that recognize the acetylated forms of the protein substrate. Detection of deacetylated protein products can be effected by scintillation proximity assay, and nonisotopic, fluorescence based assays (reviewed by Borra and Denu, 2004, Methods in Enzymology 376:171-87).

This assay can be used, by one ordinarily skilled in the art, to determine which of the antagonists listed below is most efficient for the purpose of implementing the various methods, preparations and articles-of-manufacture of the present invention which are further described hereinafter. To determine most effective concentrations and exposure time for achieving optimal results with stem cells of different origins.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed.

(1994); "Current Protocols in immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Cells and Culture Conditions

Sample collection and purification—Cells were obtained from umbilical cord blood (CB) after a normal full-term delivery (informed consent was given). Samples were collected and processed within 12 hours postpartum. Blood was mixed with 3% Gelatin (Sigma, St. Louis, Mo.) and let sedimented for 30 minutes to remove most red blood cells (RBC). The leukocyte-rich fraction was harvested and layered on Ficoll-Hypaque gradient (1.077 g/mL; Sigma), and centrifuged at 400 g for 30 minutes. The mononuclear cells in the interface layer was then collected, washed three times, and resuspended in phosphate-buffered saline (PBS, Biological Industries) containing 0.5% bovine serum albumin (BSA, Fraction V; Sigma).

Purification of CDD133+ and CD34+ cells—To purify CDD133+ or CD34$^+$ cells, the mononuclear cell fraction was subjected to two cycles of immuno-magnetic separation using the "MiniMACS or Climax CD34 progenitor cell isolation kit" (Miltenyi Biotec, Aubun, Calif.) following the manufacturer's recommendations. The purity of the CD34$^+$ population obtained ranged from 95% to 98% as evaluated by flow cytometry (see below).

Some experiments were performed with CB derived cells negatively selected against 12 lineage specific cell surface antigens including CD38 (StemCell Technologies, Vancouver, Canada). This procedure yields a highly purified population of CD34+CD38− cells [Thomas T E, Fairhurst M A, Lansdorp P M Rapid single step immunomagnetic isolation of highly enriched primitive human hematopoietic progenitors. Blood 90 Suppl. 1 347b, 1997 (abst)].

Some experiments were initiated as well with the entire MNC fraction.

Ex vivo expansion of CD34$^+$ cells—Purified CD34$^+$ cells were cultured in 24-well Costar Cell Culture Clusters (Corning Inc. Corning, N.Y.) or culture bags at $10^4$ cells/mL in alpha medium supplemented with 10% fetal bovine serum (FBS) (Biological Industries) and the following human recombinant cytokines: Thrombopoietin (TPO), interleukin-6 (IL-6) and FLT-3 ligand, at final concentration of 50 ng/mL each +/− IL-3 at 20 ng/ml (all from Perpo Tech, Inc. Rocky Hill, N.J.), with and without Nicotinamide or Sirtinol or Splitomicin. The cultures were incubated at 37° C. in humidified atmosphere of 5% $CO_2$ in air.

At weekly intervals, cell cultures were semi-depopulated and supplemented with fresh medium, serum and cytokines. At various time points, cells were harvested, counted following staining with trypan blue, and cell morphology was determined on cytospin (Shandon, UK)-prepared smears stained with May-Grunwald/Giemsa solutions.

Two phase culture system—Purified CD34+ cells were cultured in culture bags (American Fluoroseal Co. Gaithersburg, Md., USA) at a concentration of $1\times10^4$ cells/ml in MEMα/10% FCS containing the following human recombinant cytokines: Thrombopoietin (TPO), interleukin-6 (IL-6), FLT-3 ligand and stem cell factor (SCF), each at a final concentration of 50 ng/ml (Perpo Tech, Inc., Rocky Hill, N.J., USA), with or without Nicotinamide or Sirtinol or Splitomicin and incubated at 37° C. in a humidified atmosphere of 5% $CO_2$ in air. Until week 3, the cultures were topped weekly with the same volume of fresh medium, Nicotinamide or Sirtinol or Splitomicin and growth factors. From week three and up to the termination of the experiments the cultures were weekly demi-depopulated and supplemented with cytokines only. Cells were counted following staining with trypan blue. At various time points, harvested cells were used to assay the content of colony forming units in culture (CFUc), enumeration of CD34+ cells following re-selection and immunophenotype analysis. Cell morphology was determined on cytospin (Shandon).

Assay for Colony Forming Units (CFU)—Cells were cloned in semi-solid, methylcellulose-containing medium supplemented with 2 IU/mL erythropoietin (Eprex, Cilag AG Int., Switzerland), stem cell factor and IL-3, both at 20 ng/mL, G-CSF and GM-CSF, both at 10 ng/mL (all from Perpo Tech). Cultures were incubated for 14 days at 37° C. in humidified atmosphere of 5% $CO_2$ in air.

Morphological Assessment

In order to characterize the resulting culture populations, aliquots of cells were deposited on a glass slide (cytocentrifuge, Shandon, Runcorn, UK), fixed and stained in May-Grunwald Giemsa.

Immunophenotyping—For immuno-phenotyping, cells were harvested, washed with phosphate buffered saline (PBS), containing 1% BSA and 0.1% sodium azide, and stained by incubation (at 4° C. for 60 min) with phycoerythrin (PE)-conjugated anti CD38 (Immunoquality Products, The Netherlands), flourescein isothiocyanate (FITC)-conjugated anti CD34 (Miltenyi Biotec) both at 5 µl per 50 µl cell suspension. The cells were then washed with the same buffer and analyzed, using FACS-calibur flow cytometer (Becton-Dickinson, Immunofluorometry systems, Mountain View, Calif.). Cells were passed at a rate of about 1000 cells/second, using saline as the sheath fluid. A 488 nm argon laser beam served as the light source for excitation. Emission of ten thousand cells was measured using logarithmic amplification and calculated using the cellQuest software. Background noise was determined using isotype control stained cells. Arithmetic Mean Fluorescence Channel (MFC) of the negative and positive populations and the stained cells to noise (S/N) ratio were calculated.

Inhibitors of enzymatic reactions catalyzed by the SIR2 family of enzyme—The compounds nicotinamide (niacinamide, nicotinicacidamide, C6H6N20, lot#111 koo27, N-0636 Sigma) nicotinamide 2'-deoxyriboside (1), 5-methylnicotinamide 2'-deoxyriboside (2), and pyridyl 2'-deoxyriboside. Chemical evidence for this intermediate is the ability of nicotinamide to rescue enzyme activity after inactivation by either 1 or 2.

Sirtinol (2-[(2-hydroxy-naphthalen-1-ylmethylene)-amino]-N-(1-phenyl-ethyl)-benzamide) (ChemBridge) and sirtinol derivatives (J. Biol. Chem., Vol. 276, Issue 42, 38837-38843, Oct. 19, 2001).

Splitomicin and splitomicin derivatives (Bedalov, A., Gatbonton, T., Irvine, W. P., Gottschling, D. E., and Simon, J. A. (2001)*Proc. Natl. Acad. Sci. U.S.A.* 98, 15113-15118).

Example 1

Figure 2:
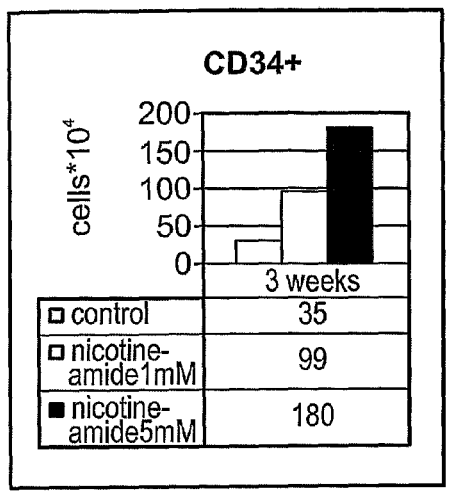
FIG. 2 is a bar graph depicting the effect of nicotineamide (1 mM, 5 mM) on expansion of CD34+ cultures.

Nicotinamide, an Inhibitor Sirt Enzymes Allows Preferential and Substantial Expansion in Ex Vivo Cultures of Late Progenitor Cells and Step/Early Progenitor Cells CD34+ cell cultures were initiated in the presence of a combination of 5 cytokines, SCF, TPO, FLt3, IL-6 and IL-3, with or without various concentrations of nicotinamide. Following three week expansion CD34+ cells were re-selected by affinity repurification method and enumerated (FIG. 2). The results demonstrated that cultures supplemented with Nicotinamide, dose response, sustain higher expansion of CD34+ cells as compared with only cytokine supplemented cultures ($180 \times 10^4$ at 5 µM nicotine amide and only $35 \times 10^4$ in only cytokine treated cultures).

Figure 5:
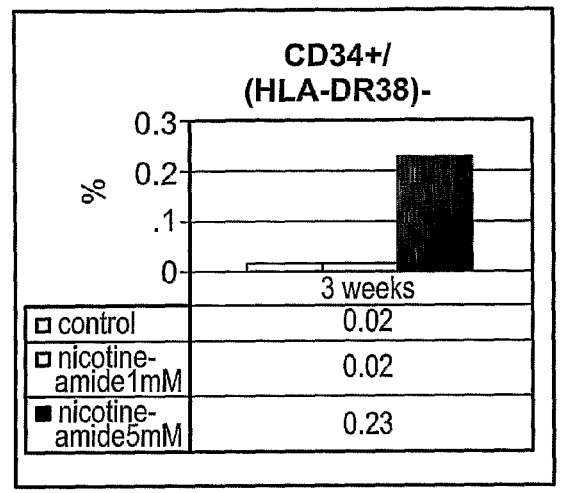
FIG. 5 is a bar graph depicting the effect of nicotineamide on expansion of CD34+/(HLA-DR38)− fraction of re-selected CD34+ cell fraction treated as in FIG. 2.
Figure 3:
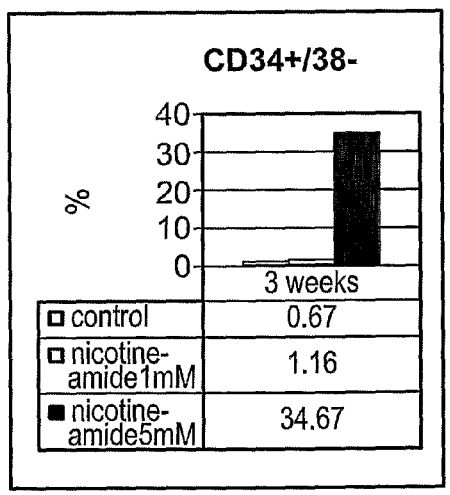
FIG. 3 is a bar graph depicting the effect of nicotineamide on expansion of CD34+/CD38− fraction of re-selected CD34+ cell fraction treated as in FIG. 2.
Figure 4:
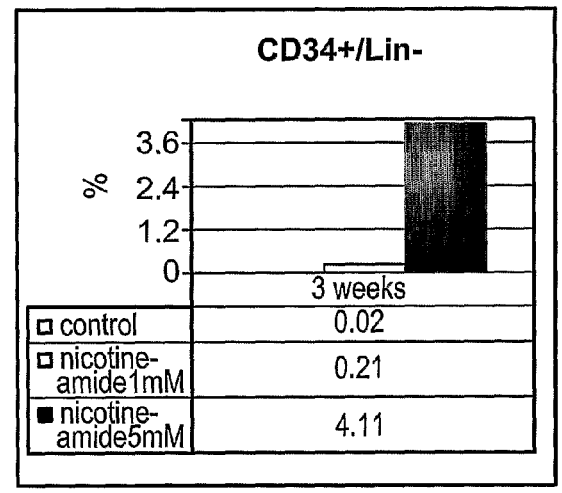
FIG. 4 is a bar graph depicting the effect of nicotineamide on expansion of CD34+/Lin− fraction of re-selected CD34+ cell fraction treated as in FIG. 2.

The highly purified, re-selected CD34+ cell fraction from a three week culture was FACS analyzed for stem/early progenitor cells: CD34+CD38− (FIG. 3), CD34+Lin−(CD3, 4, 19, 38, 33, 14 and 15 minus, FIG. 4) as well as for the percentages of CD38-HLA-DR minus cells (FIG. 5). The results indicated that nicotinamide treated cultures contained a significantly highly proportion of Stem early progenitor cells as compared to only cytokine treated cultures. For example, at 5 uM nicotinamide the percentages of CD34+ Lin− cells were 4.11 whereas in control cultures only 0.02%, the percentages of CD34+CD38− cells were 34.6 in nicotinamide cultures and only 0.67 in control.

Figure 6A:
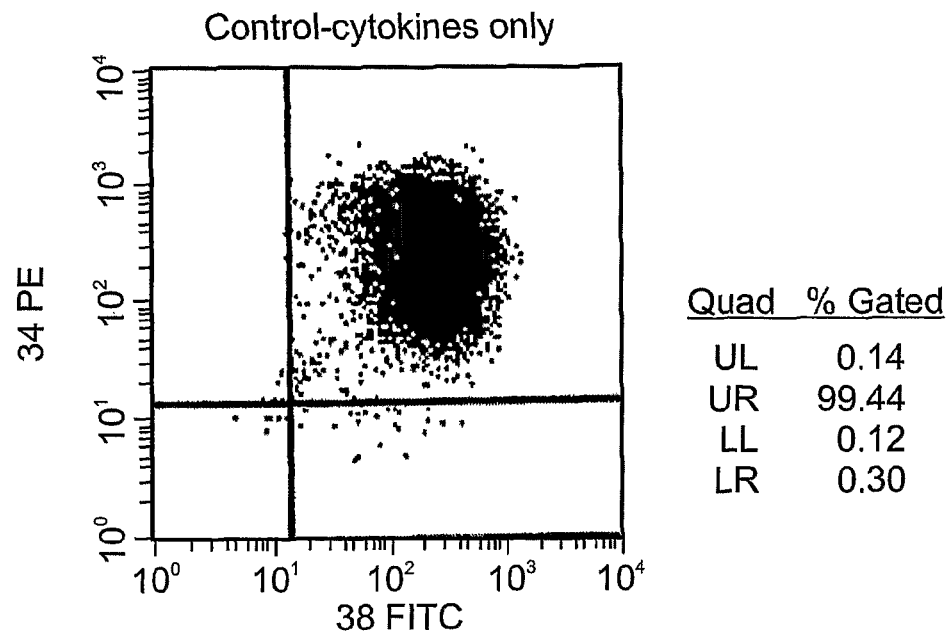
FIGS. 6a-c are dot plots presenting FACS analyses showing stem-cell/progenitor cell population distribution in the presence (lower panels) or absence (upper panels) of Nicotinamide (5 mM).
Figure 6A:
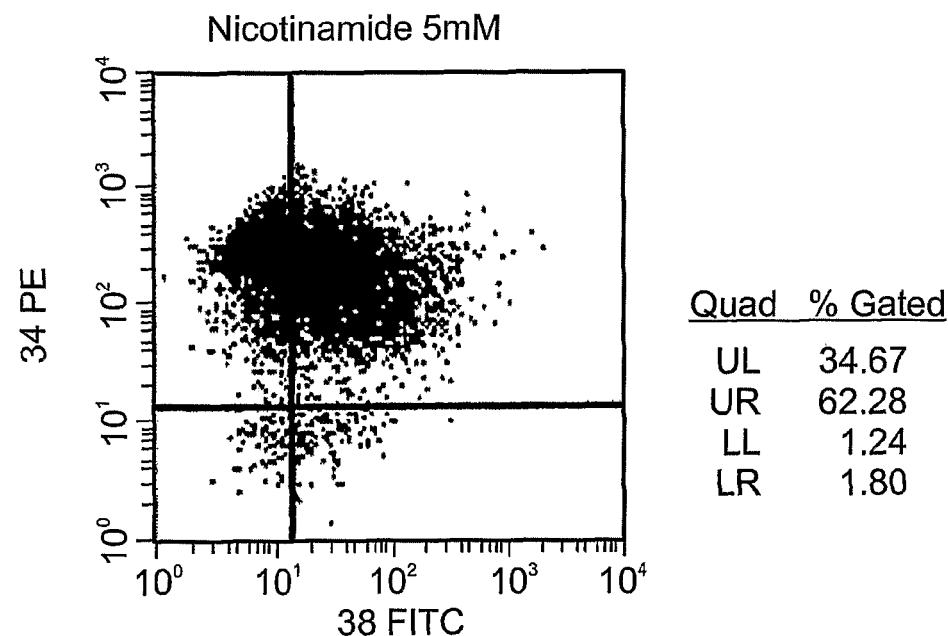
Figure 6B:
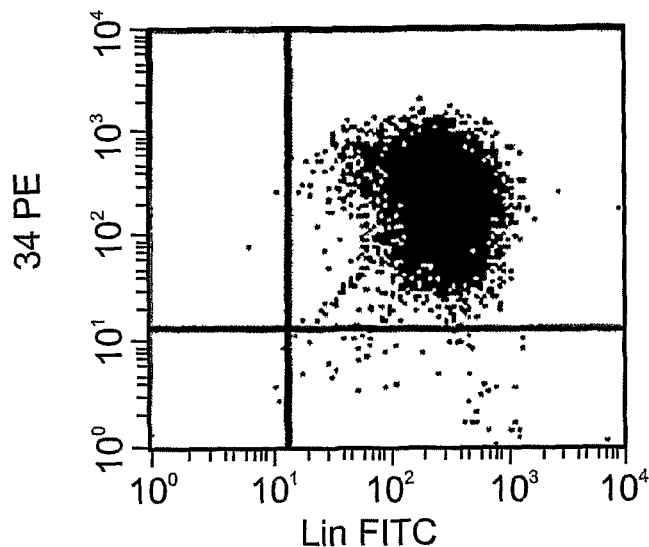
Figure 6B:
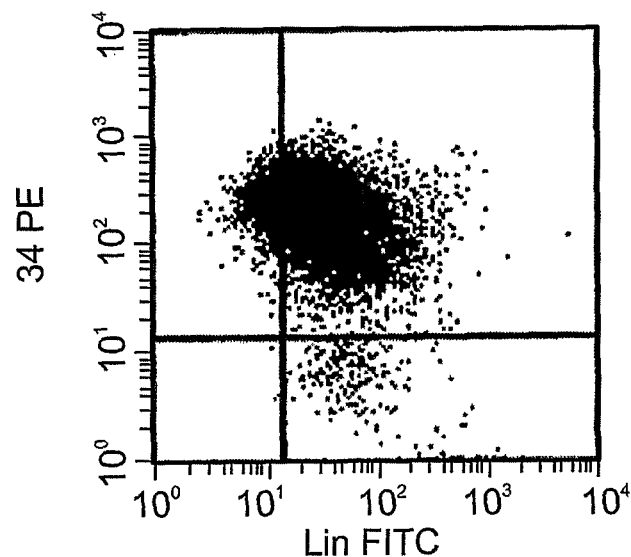
Figure 6C:
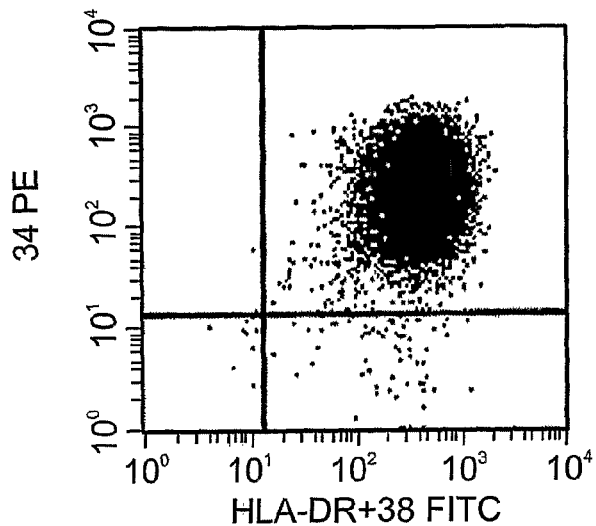
Figure 6C:
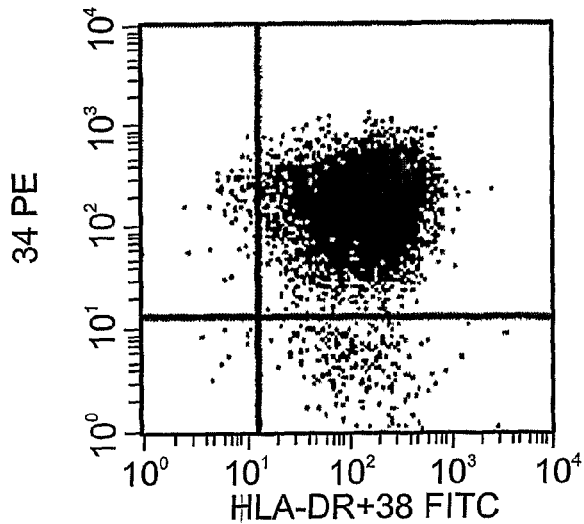

FIGS. 6*a-c* demonstrate representative dot plots of FACS analyses conducted on re-selected CD34+ cells from a three week culture: FIG. 6*a* the cells were stained with CD34+ PE and CD38FITC. The CD34+CD38− cells are shown in the upper left part of the plot. FIG. 6*b*, the cells were stained with CD34(PE) and Lin(38, 33, 4, 3, 15, 14, 19, 61) (FITC). The CD34+Lin− cells are shown in the upper left part of the plot. FIG. 6*c*, the cells were stained for 34PE and HLA-DR and CD38 FITC. The CD34+/CD38− HLA-DR− cells are shown in the upper left part of the plot.

In an attempt to elucidate the mechanism of Sirtuin inhibitors, a two-phase culture procedure was employed: An initial three-week treatment phase, during which the cultures were supplemented with both; an inhibitor compound and cytokines, and an assay phase, from week 3 onward, during which the inhibitors were removed and the cultures were supplemented with cytokines alone. The results indicate that long-term CFUc and CD34+ cell expansion in the assay phase persists even in cultures supplemented with inhibitory compounds during the first three-week treatment phase only. These findings suggest inhibition of lineage-specific differentiation or modulation of the self-renewal potential of a CD34+ cell subset.

Figure 7A:
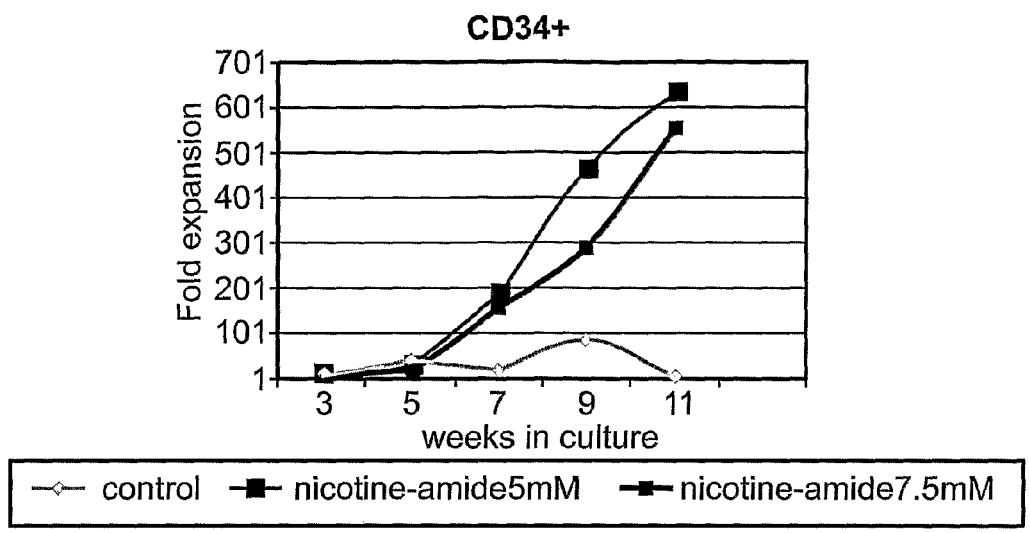
FIGS. 7a-b are line graphs depicting long-term CD34+ cell expansion (FIG. 7a) and CFUc (FIG. 7b) cell potential of cultures treated according to the two-phase culture system in the absence (indicated by diamonds) or presence of nicotineamide (indicated by squares; 5 mM fine-line, 7.5 mM solid line).
Figure 7B:
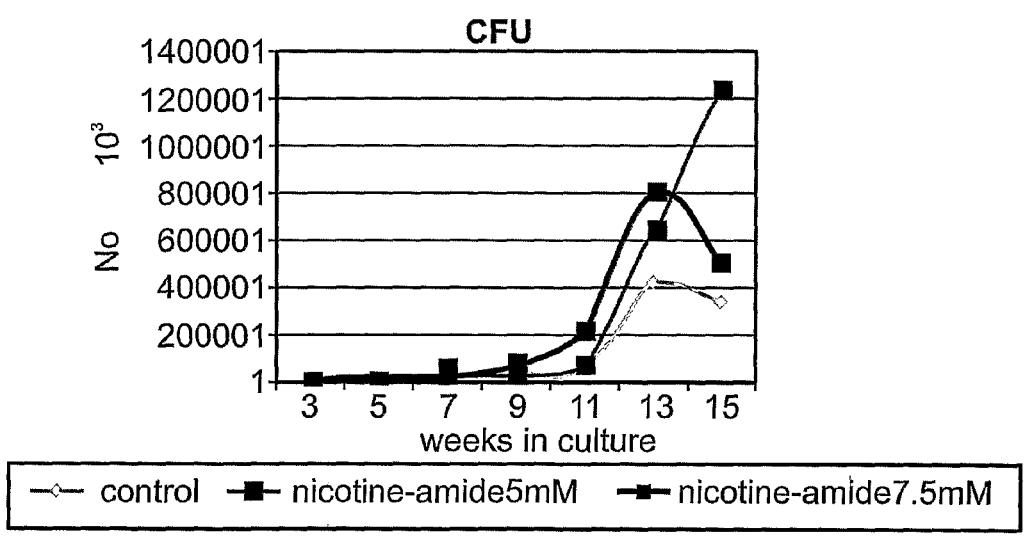

FIGS. 7*a-b* demonstrate long-term CD34+ (FIG. 7*a*) and CFUc (FIG. 7*b*) cell potential of cultures treated according to the two-phase culture system.

In conclusion, nicotinamide, an inhibitor Sir2 enzymes allows preferential and substantial expansion in ex vivo cultures of late progenitor cells (CD34+ cells), as well as that of stem/early progenitor cells (CD34+CD38−, CD34+Lin−, CD34+/CD38− HLA-DR−) as compared with only cytokine treated cultures.

Example 2

Splitomicin, a Specific Sir2 Inhibitor, Allows Long-Term Differentiation-Less Expansion of CD34+ Cell Cultures The effect of a Sir2 inhibitor on the differentiation-less expansion of CD34+ cells was determined Cell culturing—Cell culturing was effected was described above. Specifically, cultures were initiated with a total of $1.2 \times 10^5$ CD34+ cells in cytokine-supplemented medium, with or without (control) 200 mM Splitomicin. From week 3 and on all cultures were supplemented with cytokines only. On week 5 cells were enumerated, numbers of CFUc were determined and CD34+ cells were re-isolated from 10 ml cultures, counted and accumulative numbers per culture were calculated.

Results

As is shown in FIGS. 8*a-c* CD34+ cultures incubated in the presence of Splitomicin exhibited more than 2 fold total cell expansion (FIG. 8*a*), of which about 30% increase in CD34+ cells (FIG. 8*b*). An increase in colony formation (as determined by CFU analysis) indicated the self-renewal potential of the cells following incubation with the Sir2 inhibitor (FIG. 8*c*). FACS analysis of 3 week treated cultures showed a differentiation-less cell expansion of the CD34+CD38− stem cell population in the presence of increasing concentrations of splitomicin (FIGS. 9*a-c*).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A method of expanding and inhibiting differentiation of a population of hematopoietic stem cells and/or hematopoietic progenitor cells, the method comprising:
   (a) providing the stem and/or progenitor cells ex vivo with conditions for cell proliferation; and
   (b) ex vivo expanding the stem and/or progenitor cells with an inhibitor of mammalian sirtuin deacetylase catalytic activity, thereby expanding and inhibiting differentiation of the population of stem and/or progenitor cells, wherein said inhibitor is selected from the group consisting of sirtinol, M15, and splitomicin.

2. The method of claim 1, wherein said sirtuin deacetylase protein is a human sirtuin.

3. The method of claim 1, wherein said conditions for cell proliferation are selected from the group consisting of a growth medium, differentiation chemical inhibitors and cytokines.

4. The method of claim 3, wherein said cytokines are selected from the group consisting of early acting cytokines and late acting cytokines.

5. The method of claim 4, wherein said early acting cytokines are selected from the group consisting of stem cell factor, FLT3 ligand, interleukin-6, thrombopoietin and interleukin-3.

6. The method of claim 4, wherein said late acting cytokines are selected from the group consisting of granulocyte colony stimulating factor, granulocyte/macrophage colony stimulating factor and erythropoietin.

7. The method of claim 1, wherein said stem and/or progenitor cells are derived from bone marrow or peripheral blood.

8. The method of claim 1, wherein said stem and/or progenitor cells are derived from neonatal umbilical cord blood.

9. The method of claim 1, wherein the population of stem and/or progenitor cells are enriched for hematopoietic stem and/or progenitor cells.

10. The method of claim 1, further comprising the step of selecting a population of stem and/or progenitor cells enriched for hematopoietic stem cells.

11. The method of claim 10, wherein said selecting is affected via CD34.

12. The method of claim 1, further comprising the step of selecting a population of stem and/or progenitor cells enriched for early hematopoietic stem/progenitor cells.

13. The method of claim 12, wherein said selection is affected via CD133.

14. The method of claim 10, wherein said mammalian sirtuin deacetylase protein is a human sirtuin1.

* * * * *

UNITED STATES PATENT AND TRADEMARK OFFICE
CERTIFICATE OF CORRECTION

| | | |
|---|---|---|
| PATENT NO. | : 8,187,876 B2 | Page 1 of 1 |
| APPLICATION NO. | : 11/631992 | |
| DATED | : May 29, 2012 | |
| INVENTOR(S) | : Tony Peled | |

It is certified that error appears in the above-identified patent and that said Letters Patent is hereby corrected as shown below:

At column 70, claim number 14, line 49, "The method of claim 10" should read --The method of claim 2--.

Signed and Sealed this
Fourteenth Day of August, 2012

David J. Kappos
*Director of the United States Patent and Trademark Office*

SEQUENCE LISTING

<160> NUMBER OF SEQ ID NOS: 62

<210> SEQ ID NO 1
<211> LENGTH: 19
<212> TYPE: DNA
<213> ORGANISM: Artificial sequence
<220> FEATURE:
<223> OTHER INFORMATION: SiRNA

<400> SEQUENCE: 1
gaagtgcctc agatattaa                                                19

<210> SEQ ID NO 2
<211> LENGTH: 19
<212> TYPE: DNA
<213> ORGANISM: Artificial sequence
<220> FEATURE:
<223> OTHER INFORMATION: SiRNA

<400> SEQUENCE: 2
acactgtggc agattgtta                                                19

<210> SEQ ID NO 3
<211> LENGTH: 19
<212> TYPE: DNA
<213> ORGANISM: Artificial sequence
<220> FEATURE:
<223> OTHER INFORMATION: SiRNA

<400> SEQUENCE: 3
taatatcctt tcagaacca                                                19

<210> SEQ ID NO 4
<211> LENGTH: 19
<212> TYPE: DNA
<213> ORGANISM: Artificial sequence
<220> FEATURE:
<223> OTHER INFORMATION: SiRNA

<400> SEQUENCE: 4
aagcgatgtt tgatattga                                                19

<210> SEQ ID NO 5
<211> LENGTH: 19
<212> TYPE: DNA
<213> ORGANISM: Artificial sequence
<220> FEATURE:
<223> OTHER INFORMATION: SiRNA

<400> SEQUENCE: 5
agcgatgttt gatattgaa                                                19

<210> SEQ ID NO 6
<211> LENGTH: 19
<212> TYPE: DNA
<213> ORGANISM: Artificial sequence
<220> FEATURE:
<223> OTHER INFORMATION: SiRNA

<400> SEQUENCE: 6
taagaccagt agcactaat                                                19

<210> SEQ ID NO 7
<211> LENGTH: 19
<212> TYPE: DNA

```
<213> ORGANISM: Artificial sequence
<220> FEATURE:
<223> OTHER INFORMATION: SiRNA

<400> SEQUENCE: 7
tctgttcggt gatgaaatt                                              19

<210> SEQ ID NO 8
<211> LENGTH: 19
<212> TYPE: DNA
<213> ORGANISM: Artificial sequence
<220> FEATURE:
<223> OTHER INFORMATION: SiRNA

<400> SEQUENCE: 8
tcctcgaaca attcttaaa                                              19

<210> SEQ ID NO 9
<211> LENGTH: 19
<212> TYPE: DNA
<213> ORGANISM: Artificial sequence
<220> FEATURE:
<223> OTHER INFORMATION: SiRNA

<400> SEQUENCE: 9
taggttaggt ggtgaatat                                              19

<210> SEQ ID NO 10
<211> LENGTH: 19
<212> TYPE: DNA
<213> ORGANISM: Artificial sequence
<220> FEATURE:
<223> OTHER INFORMATION: SiRNA

<400> SEQUENCE: 10
gaagcctgat atcgtcttt                                              19

<210> SEQ ID NO 11
<211> LENGTH: 19
<212> TYPE: DNA
<213> ORGANISM: Artificial sequence
<220> FEATURE:
<223> OTHER INFORMATION: SiRNA

<400> SEQUENCE: 11
ccagaggcca tctttgaga                                              19

<210> SEQ ID NO 12
<211> LENGTH: 19
<212> TYPE: DNA
<213> ORGANISM: Artificial sequence
<220> FEATURE:
<223> OTHER INFORMATION: SiRNA

<400> SEQUENCE: 12
gatcagctat ttcaagaaa                                              19

<210> SEQ ID NO 13
<211> LENGTH: 19
<212> TYPE: DNA
<213> ORGANISM: Artificial sequence
<220> FEATURE:
<223> OTHER INFORMATION: SiRNA

<400> SEQUENCE: 13
gctacacgca gaacataga                                              19
```

```
<210> SEQ ID NO 14
<211> LENGTH: 19
<212> TYPE: DNA
<213> ORGANISM: Artificial sequence
<220> FEATURE:
<223> OTHER INFORMATION: SiRNA

<400> SEQUENCE: 14
cctcgccaag gaactctat                                                    19

<210> SEQ ID NO 15
<211> LENGTH: 19
<212> TYPE: DNA
<213> ORGANISM: Artificial sequence
<220> FEATURE:
<223> OTHER INFORMATION: SiRNA

<400> SEQUENCE: 15
gtcgcagagt catctgttt                                                    19

<210> SEQ ID NO 16
<211> LENGTH: 19
<212> TYPE: DNA
<213> ORGANISM: Artificial sequence
<220> FEATURE:
<223> OTHER INFORMATION: SiRNA

<400> SEQUENCE: 16
cggcaccttc tacacatca                                                    19

<210> SEQ ID NO 17
<211> LENGTH: 19
<212> TYPE: DNA
<213> ORGANISM: Artificial sequence
<220> FEATURE:
<223> OTHER INFORMATION: SiRNA

<400> SEQUENCE: 17
acatggactt cctgcggaa                                                    19

<210> SEQ ID NO 18
<211> LENGTH: 19
<212> TYPE: DNA
<213> ORGANISM: Artificial sequence
<220> FEATURE:
<223> OTHER INFORMATION: SiRNA

<400> SEQUENCE: 18
caacgtcact cactacttt                                                    19

<210> SEQ ID NO 19
<211> LENGTH: 19
<212> TYPE: DNA
<213> ORGANISM: Artificial sequence
<220> FEATURE:
<223> OTHER INFORMATION: SiRNA

<400> SEQUENCE: 19
ccaacgtcac tcactactt                                                    19

<210> SEQ ID NO 20
<211> LENGTH: 19
<212> TYPE: DNA
<213> ORGANISM: Artificial sequence
<220> FEATURE:
<223> OTHER INFORMATION: SiRNA
```

-continued

```
<400> SEQUENCE: 20
ttcgagtatt aaaggtgga                                                  19

<210> SEQ ID NO 21
<211> LENGTH: 19
<212> TYPE: DNA
<213> ORGANISM: Artificial sequence
<220> FEATURE:
<223> OTHER INFORMATION: SiRNA

<400> SEQUENCE: 21
acgtcactca ctactttct                                                  19

<210> SEQ ID NO 22
<211> LENGTH: 19
<212> TYPE: DNA
<213> ORGANISM: Artificial sequence
<220> FEATURE:
<223> OTHER INFORMATION: SiRNA

<400> SEQUENCE: 22
acctgcacag tctgccaaa                                                  19

<210> SEQ ID NO 23
<211> LENGTH: 19
<212> TYPE: DNA
<213> ORGANISM: Artificial sequence
<220> FEATURE:
<223> OTHER INFORMATION: SiRNA

<400> SEQUENCE: 23
tgagctttgc gttgacttt                                                  19

<210> SEQ ID NO 24
<211> LENGTH: 19
<212> TYPE: DNA
<213> ORGANISM: Artificial sequence
<220> FEATURE:
<223> OTHER INFORMATION: SiRNA

<400> SEQUENCE: 24
aaaggccgtt ggatcgcaa                                                  19

<210> SEQ ID NO 25
<211> LENGTH: 19
<212> TYPE: DNA
<213> ORGANISM: Artificial sequence
<220> FEATURE:
<223> OTHER INFORMATION: SiRNA

<400> SEQUENCE: 25
aagatgagct ttgcgttga                                                  19

<210> SEQ ID NO 26
<211> LENGTH: 19
<212> TYPE: DNA
<213> ORGANISM: Artificial sequence
<220> FEATURE:
<223> OTHER INFORMATION: SiRNA

<400> SEQUENCE: 26
agatgagctt tgcgttgac                                                  19

<210> SEQ ID NO 27
<211> LENGTH: 19
<212> TYPE: DNA
```

```
<213> ORGANISM: Artificial sequence
<220> FEATURE:
<223> OTHER INFORMATION: SiRNA

<400> SEQUENCE: 27
gagttacagc gcttcatca                                              19

<210> SEQ ID NO 28
<211> LENGTH: 19
<212> TYPE: DNA
<213> ORGANISM: Artificial sequence
<220> FEATURE:
<223> OTHER INFORMATION: SiRNA

<400> SEQUENCE: 28
ttcgtaggct ggcctcaat                                              19

<210> SEQ ID NO 29
<211> LENGTH: 19
<212> TYPE: DNA
<213> ORGANISM: Artificial sequence
<220> FEATURE:
<223> OTHER INFORMATION: SiRNA

<400> SEQUENCE: 29
tcggaaagct gtactggtt                                              19

<210> SEQ ID NO 30
<211> LENGTH: 19
<212> TYPE: DNA
<213> ORGANISM: Artificial sequence
<220> FEATURE:
<223> OTHER INFORMATION: SiRNA

<400> SEQUENCE: 30
gcaagagcgt ttccaagtc                                              19

<210> SEQ ID NO 31
<211> LENGTH: 19
<212> TYPE: DNA
<213> ORGANISM: Artificial sequence
<220> FEATURE:
<223> OTHER INFORMATION: SiRNA

<400> SEQUENCE: 31
gatccatggt agcttattt                                              19

<210> SEQ ID NO 32
<211> LENGTH: 19
<212> TYPE: DNA
<213> ORGANISM: Artificial sequence
<220> FEATURE:
<223> OTHER INFORMATION: SiRNA

<400> SEQUENCE: 32
atccatggta gcttattta                                              19

<210> SEQ ID NO 33
<211> LENGTH: 19
<212> TYPE: DNA
<213> ORGANISM: Artificial sequence
<220> FEATURE:
<223> OTHER INFORMATION: SiRNA

<400> SEQUENCE: 33
tccatggtag cttatttaa                                              19
```

```
<210> SEQ ID NO 34
<211> LENGTH: 19
<212> TYPE: DNA
<213> ORGANISM: Artificial sequence
<220> FEATURE:
<223> OTHER INFORMATION: SiRNA

<400> SEQUENCE: 34
aaagtggtgt tccgacctt                                                    19

<210> SEQ ID NO 35
<211> LENGTH: 19
<212> TYPE: DNA
<213> ORGANISM: Artificial sequence
<220> FEATURE:
<223> OTHER INFORMATION: SiRNA

<400> SEQUENCE: 35
agatccatgg tagcttatt                                                    19

<210> SEQ ID NO 36
<211> LENGTH: 19
<212> TYPE: DNA
<213> ORGANISM: Artificial sequence
<220> FEATURE:
<223> OTHER INFORMATION: SiRNA

<400> SEQUENCE: 36
gttcaagtat ggcagattt                                                    19

<210> SEQ ID NO 37
<211> LENGTH: 19
<212> TYPE: DNA
<213> ORGANISM: Artificial sequence
<220> FEATURE:
<223> OTHER INFORMATION: SiRNA

<400> SEQUENCE: 37
agctggtgtt agtgcagaa                                                    19

<210> SEQ ID NO 38
<211> LENGTH: 19
<212> TYPE: DNA
<213> ORGANISM: Artificial sequence
<220> FEATURE:
<223> OTHER INFORMATION: SiRNA

<400> SEQUENCE: 38
tggtgttccg accttcaga                                                    19

<210> SEQ ID NO 39
<211> LENGTH: 19
<212> TYPE: DNA
<213> ORGANISM: Artificial sequence
<220> FEATURE:
<223> OTHER INFORMATION: SiRNA

<400> SEQUENCE: 39
agtggtgttc cgaccttca                                                    19

<210> SEQ ID NO 40
<211> LENGTH: 19
<212> TYPE: DNA
<213> ORGANISM: Artificial sequence
<220> FEATURE:
<223> OTHER INFORMATION: SiRNA
```

```
<400> SEQUENCE: 40
gctggtgtta gtgcagaaa                                              19

<210> SEQ ID NO 41
<211> LENGTH: 19
<212> TYPE: DNA
<213> ORGANISM: Artificial sequence
<220> FEATURE:
<223> OTHER INFORMATION: SiRNA

<400> SEQUENCE: 41
ggaagaatgt gccaagtgt                                              19

<210> SEQ ID NO 42
<211> LENGTH: 19
<212> TYPE: DNA
<213> ORGANISM: Artificial sequence
<220> FEATURE:
<223> OTHER INFORMATION: SiRNA

<400> SEQUENCE: 42
ccaagtgtaa gacgcagta                                              19

<210> SEQ ID NO 43
<211> LENGTH: 19
<212> TYPE: DNA
<213> ORGANISM: Artificial sequence
<220> FEATURE:
<223> OTHER INFORMATION: SiRNA

<400> SEQUENCE: 43
gcatccatgg ctacgttga                                              19

<210> SEQ ID NO 44
<211> LENGTH: 19
<212> TYPE: DNA
<213> ORGANISM: Artificial sequence
<220> FEATURE:
<223> OTHER INFORMATION: SiRNA

<400> SEQUENCE: 44
taagacgcag tacgtccga                                              19

<210> SEQ ID NO 45
<211> LENGTH: 19
<212> TYPE: DNA
<213> ORGANISM: Artificial sequence
<220> FEATURE:
<223> OTHER INFORMATION: SiRNA

<400> SEQUENCE: 45
gtgccaagtg taagacgca                                              19

<210> SEQ ID NO 46
<211> LENGTH: 19
<212> TYPE: DNA
<213> ORGANISM: Artificial sequence
<220> FEATURE:
<223> OTHER INFORMATION: SiRNA

<400> SEQUENCE: 46
tccatggcta cgttgacga                                              19

<210> SEQ ID NO 47
<211> LENGTH: 19
<212> TYPE: DNA
```

```
<213> ORGANISM: Artificial sequence
<220> FEATURE:
<223> OTHER INFORMATION: SiRNA

<400> SEQUENCE: 47
gccaagtgta agacgcagt                                                    19

<210> SEQ ID NO 48
<211> LENGTH: 19
<212> TYPE: DNA
<213> ORGANISM: Artificial sequence
<220> FEATURE:
<223> OTHER INFORMATION: SiRNA

<400> SEQUENCE: 48
tctggcagtc ttccagtgt                                                    19

<210> SEQ ID NO 49
<211> LENGTH: 19
<212> TYPE: DNA
<213> ORGANISM: Artificial sequence
<220> FEATURE:
<223> OTHER INFORMATION: SiRNA

<400> SEQUENCE: 49
catccatggc tacgttgac                                                    19

<210> SEQ ID NO 50
<211> LENGTH: 19
<212> TYPE: DNA
<213> ORGANISM: Artificial sequence
<220> FEATURE:
<223> OTHER INFORMATION: SiRNA

<400> SEQUENCE: 50
caagtgtaag acgcagtac                                                    19

<210> SEQ ID NO 51
<211> LENGTH: 19
<212> TYPE: DNA
<213> ORGANISM: Artificial sequence
<220> FEATURE:
<223> OTHER INFORMATION: SiRNA

<400> SEQUENCE: 51
atccatggct acgttgacg                                                    19

<210> SEQ ID NO 52
<211> LENGTH: 19
<212> TYPE: DNA
<213> ORGANISM: Artificial sequence
<220> FEATURE:
<223> OTHER INFORMATION: SiRNA

<400> SEQUENCE: 52
ccaaatactt ggtcgtcta                                                    19

<210> SEQ ID NO 53
<211> LENGTH: 19
<212> TYPE: DNA
<213> ORGANISM: Artificial sequence
<220> FEATURE:
<223> OTHER INFORMATION: SiRNA

<400> SEQUENCE: 53
cgaagcttta catcgtgaa                                                    19
```

```
<210> SEQ ID NO 54
<211> LENGTH: 19
<212> TYPE: DNA
<213> ORGANISM: Artificial sequence
<220> FEATURE:
<223> OTHER INFORMATION: SiRNA

<400> SEQUENCE: 54
gtccggaacg ccaaatact                                                    19

<210> SEQ ID NO 55
<211> LENGTH: 19
<212> TYPE: DNA
<213> ORGANISM: Artificial sequence
<220> FEATURE:
<223> OTHER INFORMATION: SiRNA

<400> SEQUENCE: 55
aaatacttgg tcgtctaca                                                    19

<210> SEQ ID NO 56
<211> LENGTH: 19
<212> TYPE: DNA
<213> ORGANISM: Artificial sequence
<220> FEATURE:
<223> OTHER INFORMATION: SiRNA

<400> SEQUENCE: 56
catgtggtgt ctcagaact                                                    19

<210> SEQ ID NO 57
<211> LENGTH: 19
<212> TYPE: DNA
<213> ORGANISM: Artificial sequence
<220> FEATURE:
<223> OTHER INFORMATION: SiRNA

<400> SEQUENCE: 57
ggccgaagct ttacatcgt                                                    19

<210> SEQ ID NO 58
<211> LENGTH: 19
<212> TYPE: DNA
<213> ORGANISM: Artificial sequence
<220> FEATURE:
<223> OTHER INFORMATION: SiRNA

<400> SEQUENCE: 58
ccgaagcttt acatcgtga                                                    19

<210> SEQ ID NO 59
<211> LENGTH: 19
<212> TYPE: DNA
<213> ORGANISM: Artificial sequence
<220> FEATURE:
<223> OTHER INFORMATION: SiRNA

<400> SEQUENCE: 59
tccggaacgc caaatactt                                                    19

<210> SEQ ID NO 60
<211> LENGTH: 19
<212> TYPE: DNA
<213> ORGANISM: Artificial sequence
<220> FEATURE:
<223> OTHER INFORMATION: SiRNA
```

```
<400> SEQUENCE: 60
tgtggtgtct cagaactgt                                                    19

<210> SEQ ID NO 61
<211> LENGTH: 19
<212> TYPE: DNA
<213> ORGANISM: Artificial sequence
<220> FEATURE:
<223> OTHER INFORMATION: SiRNA

<400> SEQUENCE: 61
caaatacttg gtcgtctac                                                    19

<210> SEQ ID NO 62
<211> LENGTH: 19
<212> TYPE: DNA
<213> ORGANISM: Artificial sequence
<220> FEATURE:
<223> OTHER INFORMATION: SiRNA

<400> SEQUENCE: 62
ggaagtgtga tgacgtcat                                                    19
```